United States Patent
Kleidon

(10) Patent No.: US 11,783,722 B2
(45) Date of Patent: Oct. 10, 2023

(54) CANNABINOID COMPOSITIONS FOR VIRTUAL AND AUGMENTED REALITY EXPERIENCES

(71) Applicant: Ojai Energetics PBC, Ojai, CA (US)

(72) Inventor: William Kleidon, Ojai, CA (US)

(73) Assignee: Ojai Energetics PBC, Ojai, CA (US)

( * ) Notice: Subject to any disclaimer, the term of this patent is extended or adjusted under 35 U.S.C. 154(b) by 0 days.

(21) Appl. No.: 17/348,941

(22) Filed: Jun. 16, 2021

(65) Prior Publication Data

US 2021/0383713 A1 Dec. 9, 2021

Related U.S. Application Data

(63) Continuation of application No. PCT/US2019/066930, filed on Dec. 17, 2019.

(60) Provisional application No. 62/781,531, filed on Dec. 18, 2018, provisional application No. 62/841,040, filed on Apr. 30, 2019.

(51) Int. Cl.
| | |
|---|---|
| *A61K 36/00* | (2006.01) |
| *G09B 9/00* | (2006.01) |
| *A61K 9/50* | (2006.01) |
| *A61K 31/05* | (2006.01) |
| *A61K 31/57* | (2006.01) |
| *A61K 36/185* | (2006.01) |
| *G06F 3/01* | (2006.01) |

(52) U.S. Cl.
CPC ............... *G09B 9/00* (2013.01); *A61K 9/50* (2013.01); *A61K 31/05* (2013.01); *A61K 31/57* (2013.01); *A61K 36/185* (2013.01); *G06F 3/011* (2013.01)

(58) Field of Classification Search
CPC ........................................................ A61K 9/50
See application file for complete search history.

(56) References Cited

U.S. PATENT DOCUMENTS

| | | | |
|---|---|---|---|
| 3,456,049 | A | 7/1969 | Hotko et al. |
| 4,729,428 | A | 3/1988 | Yasutake et al. |
| 7,482,152 | B2 | 1/2009 | Ramasubramanian |
| 2006/0051416 | A1 | 3/2006 | Rastogi et al. |
| 2007/0065512 | A1 | 3/2007 | Dedhiya et al. |
| 2016/0183409 | A1 | 6/2016 | Zhou et al. |
| 2017/0172977 | A1* | 6/2017 | Kleidon ................ A61P 9/00 |
| 2017/0312308 | A1 | 11/2017 | Meloni et al. |

FOREIGN PATENT DOCUMENTS

| | | |
|---|---|---|
| WO | WO-2014100231 A1 | 6/2014 |
| WO | WO-2017218846 A1 | 12/2017 |
| WO | WO-2019234743 A1 | 12/2019 |
| WO | WO-2020131921 A1 | 6/2020 |

OTHER PUBLICATIONS

Zuurman, Effect of intrapulmonary tetrahydrocannabinol administration in humans. Journal of psychopharmacology (Oxford, England), (Sep. 2008) vol. 22, No. 7, pp. 707-716 (Year: 2008).*
Klumpers et al, Manipulating brain connectivity with delta(9)-tetrahydrocannabinol: A pharmacological resting state FMRI study. NeuroImage, (Nov. 15, 2012) vol. 63, No. 3, pp. 1701-1711 (Year: 2012).*
International search report with written opinion dated Mar. 4, 2020 for PCT/US2019/066930.
Turner, B. Sex, drugs, and driving: the effects of marijuana. May 15, 2007. PhD (Doctor of Philosophy) thesis. University of Iowa, https://doi.org/10.17077/etd.jqp9pxp7. (106 pages).
Bond, et al. The use of analogue scales in rating subjective feelings. British Journal of Medical Psychology. Aug. 31, 1974. vol. 47, Iss: 3, pp. 211-218.
Freeman, et al. How cannabis causes paranoia: using the intravenous administration of Δ9-tetrahydrocannabinol (THC) to identify key cognitive mechanisms leading to paranoia. Schizophr Bull. Mar. 2015;41(2):391-399. doi: 10.1093/schbul/sbu098. Epub Jul. 15, 2014.
Weinstein, et al. A study investigating the acute dose-response effects of 13 mg and 17 mg Delta 9-tetrahydrocannabinol on cognitive-motor skills, subjective and autonomic measures in regular users of marijuana. J Psychopharmacol. Jun. 2008;22(4):441-51. doi: 10.1177/0269881108088194.
Weinstein, et al. Brain imaging study of the acute effects of Delta9-tetrahydrocannabinol (THC) on attention and motor coordination in regular users of marijuana. Psychopharmacology (Berl). Jan. 2008;196(1):119-131. doi: 10.1007/s00213-007-0940-7. Epub Sep. 26, 2007.
GB Application No. GB2109480.0, Examination Report dated Jul. 26, 2023.

* cited by examiner

*Primary Examiner* — Qiuwen Mi
(74) *Attorney, Agent, or Firm* — Wilson Sonsini Goodrich & Rosati

(57) ABSTRACT

The present invention relates to a method for subjecting a subject to an augmented reality (AR) or virtual reality (VR) experience. The method may comprise administering to the subject a composition comprising a cannabinoid compound. The method may comprise, subsequent to the administration of the composition comprising the cannabinoid compound, using an AR or VR device to subject the subject to an AR or VR experience. The method may comprise detecting a response of the subject to the AR or VR experience and the composition comprising the cannabinoid compound.

15 Claims, 13 Drawing Sheets

CANNABINOID COMPOSITIONS FOR VIRTUAL AND AUGMENTED REALITY EXPERIENCES

CROSS-REFERENCE

This application is a Continuation Application of International Application No. PCT/US2019/066930, filed Dec. 17, 2019, which claims the benefit of U.S. Patent Application No. 62/781,531, filed Dec. 18, 2018, and U.S. Patent Application No. 62/841,040, filed Apr. 30, 2019, each of which is entirely incorporated herein by reference.

BACKGROUND

Augmented reality (AR) or virtual reality (VR) can be a simulation (e.g., a computer-generated simulation) of one or more perceptual information (visual, auditory, haptic, somatosensory, and/or olfactory modalities) that can be interacted with in a seemingly real or physical way by a person using one or more electronic devices. Examples of the electronic devices include a helmet or glasses with a screen inside, as well as clothing (e.g., gloves, shoes, shirts, etc.) fitted with one or more sensors.

AR or VR can be used in multiple applications including, for example, entertainment (e.g., video games, cinema, etc.), medicine (e.g., anxiety disorder treatment, pain management, etc.), and education (e.g., surgery training, space training, etc.). In some cases, AR or VR can be used to treat mental disorders, such as post-traumatic stress disorder (PTSD).

SUMMARY

There remains a substantial need for complementing and/or improving AR or VR experiences. Provided are systems, methods, and compositions that can improve AR or VR experiences by providing one or more physical stimulants (e.g., one or more drugs) in the VR or AR experiences. Such stimulants may provide an enhanced or additional stimulus in addition to those provided by the traditional VR or AR experience (e.g., visual stimuli, auditory stimuli, haptic stimuli, etc.).

An aspect of the present disclosure provides a method for subjecting a subject to an augmented reality (AR) or virtual reality (VR) experience, comprising: (a) administering to the subject a composition comprising a cannabinoid compound; (b) subsequent to (a), using an AR or VR device to subject the subject to an AR or VR experience; and (c) detecting a response of the subject to the AR or VR experience.

In some embodiments, the subject suffers or is suspected of suffering from one or more health conditions. In some embodiments, the one or more health conditions comprise one or more mental disorders selected from the group consisting of: anxiety disorder, mood disorder, psychotic disorder, eating disorder, impulsive control and addition disorder, personality disorder, obsessive-compulsive disorder, post-traumatic stress disorder, stress response syndrome, dissociative disorder, factitious disorder, tic disorder, and addiction.

In some embodiments, the AR or VR experience is based at least in part on a memory of a historical event of the user.

In some embodiments, the response comprises reprogramming of one or more cells of the subject. In some embodiments, the response comprises an epigenetic modification of a polynucleotide of the subject. In some embodiments, the epigenetic modification comprises DNA methylation and/or histone modification. In some embodiments, the response comprises a change in a neural network of the subject.

In some embodiments, the method further comprises subjecting the subject to emotional freedom technique (EFT) and/or eye-movement desensitization and reprocessing (EMDR).

In some embodiments, the composition comprises a plurality of microcapsules, wherein an individual microcapsule of the plurality comprises (a) at least one cannabinoid compound and/or (b) at least one terpene compound. In some embodiments, the composition comprises a plurality of microcapsules, wherein an individual microcapsule of the plurality comprises (a) at least one cannabinoid compound and (b) at least one terpene compound. In some embodiments, an individual microcapsule of the plurality comprises at least one cannabinoid compound, wherein the plurality of microcapsules are not liposomes or micelles.

In some embodiments, the cannabinoid compound comprises cannabidiol (CBD).

In some embodiments, the composition is in a liquid composition. In some embodiments, the composition is in a solid composition.

In some embodiments, the method further comprises orally administering the composition to the subject. In some embodiments, the method further comprises topically administering the composition to the subject.

In some embodiments, the method further comprises, subsequent to the detecting the response, administering to the subjected an adjusted dosage of the composition, wherein the adjusted dosage is determined at least in part on the response.

Another aspect of the present disclosure provides a method for subjecting a subject to an interactive experience, comprising: (a) administering to the subject a composition comprising a cannabinoid compound; (b) subsequent to or during (a), providing an interactive stimulation to the subject, wherein the interactive stimulation comprises a sensory stimulation; and (c) detecting a response of the subject to the interactive stimulation.

In some embodiments, the sensory stimulation comprises a visual stimulation. In some embodiments, the visual stimulation exposes the subject to a light for a predetermined duration, for a predetermined frequency, or at a predetermined wavelength or range of wavelengths. In some embodiments, the visual stimulation exposes the subject to a light for a predetermined duration, for a predetermined frequency, and at a predetermined wavelength or range of wavelengths. In some embodiments, the light is provided by a laser.

In some embodiments, the sensory stimulation comprises a temperature change or a pressure change. In some embodiments, the sensory stimulation comprises a temperature change and a pressure change.

In some embodiments, the sensory stimulation is provided in an immersive chamber. In some embodiments, the sensory stimulation comprises an auditory stimulation. In some embodiments, the sensory stimulation comprises a haptic stimulation.

In some embodiments, the sensory stimulation is provided as part of a VR or AR experience.

Another aspect of the present disclosure provides a method for subjecting a subject to an augmented reality (AR) or virtual reality (VR) experience, which subject has been administered or is being administered a composition comprising a cannabinoid compound, wherein the method comprises: (a) using an AR or VR device to subject the subject to the AR or VR experience; and (b) detecting a response of the subject to the AR or VR experience.

Another aspect of the present disclosure provides a system for subjecting a subject to an augmented reality (AR) or virtual reality (VR) experience, which subject has been administered or is being administered a composition comprising a cannabinoid compound, wherein the system comprises one or more computer processors that are individually or collectively programmed to (a) use an AR or VR device to subject the subject to the AR or VR experience; and (b) detect a response of the subject to the AR or VR experience.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1A:
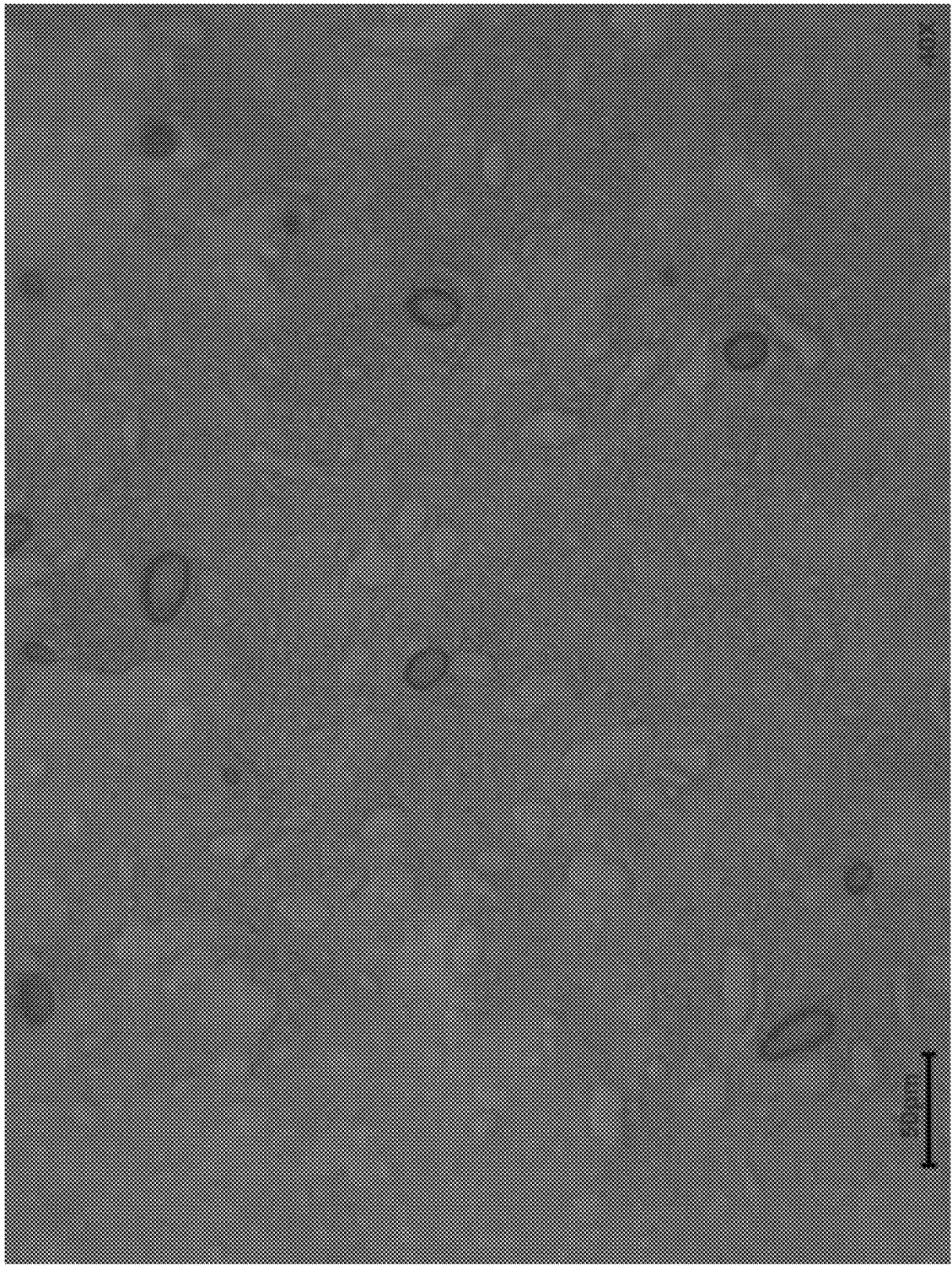
FIG. 1A shows an example of a microscope image of an unprocessed composition of quillaja extract, hemp oil, and water at 400× magnification.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The terms "augmented reality" (AR) or "virtual reality" (VR), as used herein, can refer to a computer-simulated environment that can simulate physical presence of a subject (e.g., a user) and/or an object (e.g., a physical object, a virtual object, etc.) in one or more places in the real world or virtual world(s). In some instances, a virtual reality may present a virtual world that comprises one or more virtual objects. The virtual world may only comprise virtual objects. In some instances, an augmented reality may present an augmented world that comprises at least one or more virtual objects and at least one or more real objects, or projections thereof. An augmented reality may be overlaid on a real world, or projections thereof. AR or VR can create or recreate sensory experiences, including taste, sight, smell, sound, touch, and the like. AR or VR systems may use a AR or VR device (e.g., a near eye display, head-mounted device, etc.) for presenting a virtual environment or augmented environment. For example, the virtual or augmented environment may be two-dimensional (2-D). The virtual or augmented environment may be three-dimensional (3-D). The AR or VR systems may provide a subject (e.g., a user) an interactive experience with the computer-simulated environment.

AR or VR can be a live direct or indirect view of a physical, real-world environment whose elements are augmented (or supplemented) by computer-generated sensory input such as sound, video, graphics or global positioning system (GPS) data. AR or VR may be a mediated reality, in which a view of reality is modified (possibly even diminished rather than augmented) by a computer.

The subject may be in one or more positions or postures, such as, for example, standing, sitting, squatting, lying, kneeling, etc., while using the AR or VR device to experience the AR or VR. The subject may be on or adjacent to an article of furniture while experiencing the AR or VR. The article of furniture can refer to a bed, crib, bassinet, chair, seat, loveseat, sofa, couch, head rest, stool, ottoman, bench, carpet, cloth, etc. The article of furniture can be intended for use in a home, an office, a medical facility (e.g., a hospital), a military base, a military training facility, or on a vehicle of transportation such as a car, truck, boat, bus, train, airplane, or the like. In some cases, at least a portion of the user may be in contact with a fluid (e.g., liquid and/or gas) while experiencing the AR or VR. In some examples, at least a portion of the user may be in a chamber (e.g., an open or enclosed chamber, such as a container) containing the fluid (e.g., water, saline, liquid nitrogen, etc.). In some instances, the user may be at least partially immersed in the fluid.

The term "near eye display," as used herein, can refer to a device which includes wearable projected displays, usually stereoscopic in the sense that each eye is presented with a slightly different field of view so as to create a 3D perception to a subject.

The term "emotional freedom technique" (EFT), as used herein, can refer to a form of counseling intervention that draws on various theories of alternative medicine including acupuncture, neuro-linguistic programming, energy medicine, and though field therapy (TFT). EFT may be used to treat one or more physical and/or psychological disorders, such as, for example, PTSD.

The term "eye movement desensitization and reprocessing" (EMDR), as used herein, can refer to a form of psychotherapy, in which a subject being treated is asked to recall distressing images while generating one type of bilateral sensory input, such as side-to-side eye movements or hand tapping. EMDR may be utilized to treat mental disorders, such as, for example, PTSD.

The term "reprogramming," as used herein, can refer to an altering or removing of one or more epigenetic modifications from a nucleus of a cell. Reprogramming can include transforming a cell from a first state to a second state, wherein the first and second states are different. In some cases, the first and second states may differ by one or more methylations of a polynucleotide or polypeptides, one or more protein expression profiles, size, volume, etc. In some cases, reprogramming may facilitate a reduction in cell fate commitment and, thus, the differentiation state of the cell as a whole. In some cases, reprogramming may facilitate an increase in cell fate commitment. In some cases, reprogramming may facilitate a transition from a first differentiated state to a second differentiated state.

The term "epigenetic modification," as used herein, can refer to a marking (e.g., a chemical marking) of a nucleotide (e.g., a polynucleotide, ribonucleic acid (RNA), deoxyribonucleic acid (DNA), a genome, etc.) by an epigenetic modifier. Epigenetic marks can include DNA methylation, as well as methylation and acetylation of proteins associated with DNA, such as histones. Parent-of-origin-specific gene expression (either from the maternal or paternal chromosome) may be observed in mammals due in part to one or more epigenetic modifications. Epigenetic modification may lead to stable gene silencing or activation. Other modifications such as the histone marks may lead to a stable or semi-stable expression state of a cell, defining the properties of a differentiated cell.

The term "about" or "nearly" as used herein refers to within +/−10%, 9%, 8%, 7%, 6%, 5%, 4%, 3%, 2%, or 1% of the designated amount.

AR or VR Experience Therapy

In an aspect, the present disclosure provides a method for subjecting a subject to an augmented reality (AR) or virtual reality (VR) experience, comprising (a) administering to the subject a composition comprising a cannabinoid compound. The method may comprise (b) subsequent to or during (a), using an AR or VR device to subject the subject to the AR or VR experience. The method may comprise (c) detecting a response of the subject to the AR or VR experience.

The subject may be a human (e.g., a user, a patient, a trainee, etc.). The subject may be a baby, adolescent, or adult. The subject may be at the age of at least 1, 2, 3, 4, 5, 10, 15, 20, 25, 30, 35, 40, 45, 50, 55, 60, 65, 70, 75, 80, 85, 90, 95, 100, or more. The subject may be at the age of at most 100, 95, 90, 85, 80, 75, 70, 65, 60, 55, 50, 45, 40, 35, 30, 25, 20, 15, 10, 5, 4, 3, 2, or 1.

The composition comprising the cannabinoid compound may be administered to the subject prior to, in conjunction with, and/or subsequent to the AR or VR experience.

In some cases, the composition comprising the cannabinoid compound may be administered to the subject at about 1 minute (min) to about 10 hours prior to the AR or VR experience. The administration of the composition comprising the cannabinoid compound may be at least about 1 min, 2 min, 3 min, 4 min, 5 min, 10 min, 20 min, 30 min, 40 min, 50 min, 1 hour, 2 hours, 3 hours, 4 hours, 5 hours, 6 hours, 7 hours, 8 hours, 9 hours, 10 hours, or more prior to the AR or VR experience. The administration of the composition comprising the cannabinoid compound may be at most about 10 hours, 9 hours, 8 hours, 7 hours, 6 hours, 5 hours, 4 hours, 3 hours, 2 hours, 1 hour, 50 min, 40 min, 30 min, 20 min, 20 min, 5 min, 4 min, 3 min, 2 min, 1 min, or less prior to the AR or VR experience.

In some cases, the composition comprising the cannabinoid compound may be administered to the subject during at least a portion of the AR or VR experience. In some cases, the composition comprising the cannabinoid compound may be administered to the subject during an entirety of the AR or VR experience. In some cases, the composition comprising the cannabinoid compound may be administered to the subject during at least 1 percent (%), 2%, 3%, 4%, 5%, 10%, 15%, 20%, 25%, 30%, 35%, 40%, 45%, 50%, 60%, 70%, 80%, 90%, 95%, or more of the duration of the AR or VR experience. In some cases, the composition comprising the cannabinoid compound may be administered to the subject during at most 100%, 90%, 80%, 70%, 60%, 50%, 45%, 40%, 35%, 30%, 25%, 20%, 15%, 10%, 9%, 8%, 7%, 6%, 5%, 4%, 3%, 2%, 1%, or less of the duration of the AR or VR experience.

In some cases, the composition comprising the cannabinoid compound may be administered to the subject at about 1 minute (min) to about 10 hours subsequent to the AR or VR experience. The administration of the composition comprising the cannabinoid compound may be at least about 1 min, 2 min, 3 min, 4 min, 5 min, 10 min, 20 min, 30 min, 40 min, 50 min, 1 hour, 2 hours, 3 hours, 4 hours, 5 hours, 6 hours, 7 hours, 8 hours, 9 hours, 10 hours, or more subsequent to the AR or VR experience. The administration of the composition comprising the cannabinoid compound may be at most about 10 hours, 9 hours, 8 hours, 7 hours, 6 hours, 5 hours, 4 hours, 3 hours, 2 hours, 1 hour, 50 min, 40 min, 30 min, 20 min, 20 min, 5 min, 4 min, 3 min, 2 min, 1 min, or less subsequent to the AR or VR experience.

In some cases, the method may further comprise, subsequent to (c), administering to the subject the same or an adjusted dosage of the composition as compared to an original dosage in (a). In some examples, subsequent to (c), the same dosage of the composition may be administered to the subject. In some examples, subsequent to (c), the adjusted dosage of the composition may be administered to the subject. The adjusted dosage may be determined at least in part on the detected response of the subject. The adjusted dosage may be higher or lower than the original dosage in (a).

The subject may be subjected to the AR or VR experience for at least about 1 min, 2 min, 3 min, 4 min, 5 min, 10 min, 20 min, 30 min, 40 min, 50 min, 1 hour, 2 hours, 3 hours, 4 hours, 5 hours, 6 hours, 7 hours, 8 hours, 9 hours, 10 hours, 12 hours, 16 hours, 20 hours, 24 hours, or more. The user may be subjected to the AR or VR experience for at most about 24 hours, 20 hours, 16 hours, 12 hours, 10 hours, 9 hours, 8 hours, 7 hours, 6 hours, 5 hours, 4 hours, 3 hours, 2 hours, 1 hour, 50 min, 40 min, 30 min, 20 min, 20 min, 5 min, 4 min, 3 min, 2 min, 1 min, or less.

The subject may be subjected to a combination of the cannabinoid administration and the AR or VR experience may be utilized as a therapy (e.g., a combinatorial therapy) for at least about 1 time, 2 times, 3 times, 4 times, 5 times, 6 times, 7 times, 8 times, 9 times, 10 times, 15 times, 20 times, 30 times, 40 times, 50 times, or more. The subject may be subjected to the combinatorial therapy for at most about 50 times, 40 times, 30 times, 20 times, 15 times, 10 times, 9 times, 8 times, 7 times, 6 times, 5 times, 4 times, 3 times, 2 times, or 1 time.

The AR or VR experience may be based at least in part on a memory of a historical event of the subject (e.g., the user). In some cases, the historical event may be a traumatic event that the user experienced or witnessed in the past. In an example, the historical event may be a combat experienced by a solider. In another example, the historical event may be an accident (e.g., a car accident) experienced by the subject. In a different example, the historical event may be a death of a family member of the subject. In some cases, the AR or VR may be based at least in part on a memory of a historical event of a different user.

The combination of the cannabinoid administration and the AR or VR experience may be utilized as a therapy (e.g., a combinatorial therapy) for the one or more health conditions of the subject. Such combinatorial therapy may treat or reduce an effect of the one or more health conditions to the subject. The one or more health conditions may comprise one or more psychological conditions and/or one or more physical conditions. Time of the cannabinoid administration, frequency of the cannabinoid administration, and/or duration of each of the cannabinoid administration may vary based at least in part on the psychological and/or physical conditions that the subject can be suffering from or can be suspected of suffering from.

The subject can suffer or can be suspected of suffering from one or more health conditions. In some cases, the one or more health conditions can comprise one or more mental disorders selected from the group consisting of: anxiety disorder, mood disorder, psychotic disorder, eating disorder, impulsive control and addition disorder, personality disorder, obsessive-compulsive disorder, PTSD, stress response syndrome, dissociative disorder, factitious disorder, tic disorder, and addiction. In some cases, the combinatorial therapy can treat or reduce an effect of the one or more mental disorders on the subject.

In some cases, the one or more health conditions can comprise one or more cognitive learning disabilities. In some cases, the one or more learning disabilities can be selected from the group consisting of: auditory processing disorder, dyscalculia, dysgraphia, dyslexia, language processing disorder, non-verbal learning disabilities, visual perceptual or visual motor deficit, attention-deficit or hyperactivity disorder (ADHD), dyspraxia, executive functioning, etc. In some cases, the combinatorial therapy can improve, enhance, accelerate, and/or prolong the subject's learning abilities.

In some cases, the combinatorial therapy can be utilized to induce the subject to enter or stay in one or more psychological states for a longer period of time relative to without such combinatorial therapy. The one or more psychological states can comprise a flow state. The term "flow state," as used herein, can refer to a mental state in which a subject is performing an activity (e.g., learning, playing sports, singing, playing a musical instrument, playing a game, performing tasks at work, etc.) with energized focus, full involvement, and/or enjoyment in performing the activity. The combinatorial therapy, as provided herein, can help the subject to begin experiencing or prolong the experience of (1) intense and/or focused concentration on a present moment or activity, (2) merging of action and awareness, (3) a loss of reflective self-consciousness, (4) a sense of personal control or agency over the situation or activity, (5) a distortion of temporal experience, in which the subject's subjective experience of time is altered, and/or (6) experience of the activity as intrinsically rewarding, also referred to as autotelic experience.

The subject may be standing while being subjected to the AR or VR experience. Alternatively or in addition to, the subject may be on or adjacent to an article of furniture while being subjected to the AR or VR experience. In some cases, at least a portion of the subject may be in contact with a fluid (e.g., liquid, gas, or vapor) while experiencing the AR or VR. In some cases, the at least the portion of the subject may be immersed in a liquid (e.g., immersed in a submersible chamber or float tank). The liquid may comprise an aqueous solution (e.g., water, saline, etc.). In some cases, the at least the portion of the subject may be in contact or surrounded by a gas or vapor (e.g., nitrogen gas, evaporated liquid nitrogen, etc.). A temperature of the fluid may be controlled during the AR or VR experience.

A temperature of the liquid may be controlled during the AR or VR experience. The temperature of the liquid may range between about 0 degrees Celsius (° C.) to about 50° C. The temperature of the liquid may be at least about 0° C., 1° C., 2° C., 3° C., 4° C., 5° C., 6° C., 7° C., 8° C., 9° C., 10° C., 15° C., 20° C., 25° C., 30° C., 35° C., 40° C., 45° C., 50° C., or more. The temperature of the liquid may be at most about 50° C., 45° C., 40° C., 35° C., 30° C., 25° C., 20° C., 15° C., 10° C., 9° C., 8° C., 7° C., 6° C., ° C., 4° C., ° C., 2° C., 1° C., or less.

The temperature of the gas or vapor may be controlled during the AR or VR experience. The temperature of the gas or vapor may range between about −110° C. to about 50° C. The temperature of the gas or vapor may be at least about −100° C., −95° C., −90° C., −85° C., −80° C., −75° C., −70° C., −65° C., −60° C., −55° C., −50° C., −45° C., −40° C., −35° C., −30° C., −25° C., −20° C., −15° C., −10° C., −5° C., 0° C., 5° C., 10° C., 15° C., 20° C., 25° C., 30° C., 35° C., 40° C., 45° C., 50° C., or more. The temperature of the gas or vapor may be at most about 50° C., 45° C., 40° C., 35° C., 30° C., 25° C., 20° C., 15° C., 10° C., 5° C., 0° C., −5° C., −10° C., −15° C., −10° C., −20° C., −30° C., −40° C., −50° C., −60° C., −70° C., −80° C., −90° C., −100° C., −110° C., or less.

In some cases, the subject may be in a chamber (e.g., open or closed chamber) while being subjected to the AR or VR experience. An ambient temperature of the chamber may be controlled during the AR or VR experience. The ambient temperature of the chamber may range from about −110° C. to about 50° C. The ambient temperature of the chamber may be at least about −110° C., −100° C., −95° C., −90° C., −85° C., −80° C., −75° C., −70° C., −65° C., −60° C., −55° C., −50° C., −45° C., −40° C., −35° C., −30° C., −25° C., −20° C., −15° C., −10° C., −5° C., 0° C., 5° C., 10° C., 15° C., 20° C., 25° C., 30° C., 35° C., 40° C., 45° C., 50° C., or more. The ambient temperature of the chamber may be at most about 50° C., 45° C., 40° C., 35° C., 30° C., 25° C., 20° C., 15° C., 10° C., 5° C., 0° C., −5° C., −10° C., −15° C., −10° C., −20° C., −30° C., −40° C., −50° C., −60° C., −70° C., −80° C., −90° C., −100° C., −110° C., or less. An example of such chamber may comprise a cryogenic chamber.

In some cases, the subject may be in a chamber (e.g., closed chamber) while being subjected to the AR or VR experience. An ambient pressure inside the chamber may be controlled during the AR or VR experience. The ambient pressure inside the chamber may range from about 100 kilopascal (kPa) to about 300 kPa. The ambient pressure inside the chamber may be at least about 100 kPa, 110 kPa, 120 kPa, 140 kPa, 160 kPa, 180 kPa, 200 kPa, 220 kPa, 230 kPa, 260 kPa, 280 kPa, 290 kPa, 300 kPa, or more. The ambient pressure inside the chamber may be at most about 300 kPa, 290 kPa, 280 kPa, 270 kPa, 260 kPa, 240 kPa, 220 kPa, 200 kPa, 180 kPa, 160 kPa, 140 kPa, 120 kPa, 110 kPa, 100 kPa, or less. An example of such chamber may comprise a pressure chamber (e.g., for a hyperbaric chamber, hyperbaric oxygen therapy chamber).

In some cases, the subject may be exposed to one or more lights while being subjected to the AR or VR experience. The exposure to the one or more lights may be a therapy to treat one or more health conditions, such as, for example, seasonal affective disorder (SAD), depression, jet lag, sleep disorders (e.g., circadian rhythm sleep disorder), dementia, bipolar disorder, atopic dermtitis, psoriasis, vitiligo, acne vulgaris, cancer, wounds, jaundice, etc. The subject may be placed on or adjacent to one or more light sources (e.g., at least 1, 2, 3, 4, 5, or more light sources; at most 5, 4, 3, 2, or 1 light source(s)) configured to provide or project the one or more lights to the subject or to a surrounding of the subject.

The one or more lights may comprise an electromagnetic radiation. The term "electromagnetic radiation," as used herein, generally refers to one or more wavelengths from the electromagnetic spectrum including, but not limited to x-rays (about 0.1 nanometers (nm) to about 10.0 nm; or about $10^{18}$ Hertz (Hz) to about $10^{16}$ Hz), ultraviolet (UV) rays (about 10.0 nm to about 380 nm; or about $8 \times 10^{16}$ Hz to about $10^{15}$ Hz), visible light (about 380 nm to about 750 nm; or about $8 \times 10^{14}$ Hz to about $4 \times 10^{14}$ Hz), infrared (IR) light (about 750 nm to about 0.1 centimeters (cm); or about $4 \times 10^{14}$ Hz to about $5 \times 10^{11}$ Hz), and microwaves (about 0.1 cm to about 100 cm; or about $10^8$ Hz to about $5 \times 10^{11}$ Hz). In some cases, the one or more light sources may provide a plurality of wavelengths from the electromagnetic radiation (e.g., light emitting diode (LED)). In some cases, the one or more light sources may provide a single individual wavelength from the electromagnetic radiation (e.g., a laser).

The combination of the cannabinoid administration and the AR or VR experience may reprogram one or more cells (e.g., a stem cell to a neuronal cell) of the subject. The reprogramming of the one or more cells may occur in one or more regions of the body of the subject, including, for example, blood, bones, heart, muscle tissues, brain, skin, etc.

The combination of the cannabinoid administration and the AR or VR experience may induce an epigenetic modification of a polynucleotide of the subject. The epigenetic modification can comprise at least 1, 2, 3, 4, 5, 6, 7, 8, 9, 10, or more epigenetic modifications. The epigenetic modification can comprise at most 10, 9, 8, 7, 6, 5, 4, 3, 2, or 1 epigenetic modification. The epigenetic modification can occur in one or more cells of the subject. The epigenetic modification may comprise DNA methylation and/or histone modification. The epigenetic modification may be temporary or permanent. The epigenetic modification may not last through a cell division. Alternatively, the epigenetic modification may last through at least 1, 2, 3, 4, 5, 6, 7, 8, 9, 10, or more cell divisions. The epigenetic modification may last through at most 10, 9, 8, 7, 6, 5, 4, 3, 2, or 1 cell division.

The combination of the cannabinoid administration and the AR or VR experience may affect the neural network of the subject. The alternation of the neural network of the subject may help maintain or change the neural network of the subject. In some cases, the chain in the neural network of the subject may comprise creation of a neuron cell (e.g., differentiation of a stem cell into a neuron cell) or death of a neuron cell. In some cases, the epigenetic modification in one or more cells of the subject may yield the change in the neural network of the subject.

In some cases, the subject may be subjected to EFT and/or EMDR. The combination of the cannabinoid administration, the AR or VR experience, the EFT, and/or EMDR may be utilized as a therapy for the one or more health conditions of the subject as provided herein.

Another aspect of the present disclosure provides cannabinoid compositions, and methods for the manufacture, delivery, and use of such compositions. The compositions of the present disclosure can comprise cannabinoids, terpenes, and/or other desirable compounds. Cannabinoid compositions can be encapsulated, including in microcapsules. Terpene compositions can be encapsulated, including in microcapsules. Cannabinoid and terpene compositions can be encapsulated, including in microcapsules. Microencapsulation can provide benefits such as shelf stability, improved bioavailability, reduced first-pass metabolism, and extended or modified release profiles (e.g., release profiles of cannabinoid and/or terpene).

In one embodiment, the present invention provides a composition comprising a plurality of microcapsules, wherein an individual microcapsule of the plurality comprises at least one cannabinoid compound and/or at least one terpene compound. The at least one terpene compound may be present in the individual microcapsule in an amount of at least about one microgram. In another embodiment, the present invention provides a composition comprising a plurality of microcapsules, wherein an individual microcapsule of the plurality comprises at least one cannabinoid compound, and wherein the microcapsules are not liposomes or micelles. In another embodiment, the present invention provides a composition comprising a plurality of microcapsules, wherein an individual microcapsule of the plurality of microcapsules comprises at least one cannabinoid compound, and wherein the composition has a shelf half-life of at least 30 days. In other embodiments, the present invention provides food products that are rich in cannabinoids, including food products with hemp oil or hemp seed oil.

Subjecting the subject to the combination of (i) the AR or VR experience and (ii) the administration of the composition that comprises the cannabinoid and/or terpene compound (e.g., at the same time, and/or in a sequential manner) can regulate a psychological state (e.g., mood) and/or physical state (e.g., pain in one or more locations of the subject's body) of the subject. The combination of (i) the AR or VR experience and (ii) the administration of the composition that comprises the cannabinoid and/or terpene compound may allow the subject to enter a particular psychological state and/or physical state. Alternatively or in addition to, the combination of (i) the AR or VR experience and (ii) the administration of the composition that comprises the cannabinoid and/or terpene compound may allow the subject to exit from a particular psychological state and/or physical state. In a different alternative or addition, the combination of (i) the AR or VR experience and (ii) the administration of the composition that comprises the cannabinoid and/or terpene compound may allow the subject to remain in a particular psychological state and/or physical state for a longer period of time, in comparison to without one or both of (i) the AR or VR experience and (ii) the administration of the composition that comprises the cannabinoid and/or terpene compound.

Subjecting the subject to the combination of (i) the AR or VR experience and (ii) the administration of the composition that comprises the cannabinoid and/or terpene compound can be used for one or more entertainment or recreational applications. The AR or VR experience may be part of the entertainment or recreational applications. The administration of the cannabinoid compound-comprising composition may allow or assist the subject to enter or experience a particular psychological state, physical state, and/or theme that is intended by the AR or VR experience. In some examples, a dose of the administration of the cannabinoid compound-comprising composition may vary during the AR or VR experience depending on the scene of the AR or VR experience. For example, a mechanism and/or dosage of administration of the cannabinoid compound-comprising composition during the AR or VR experience may be synchronized with the content of the AR or VR experience. The administration may be synchronized with the timeline of the AR or VR experience. The mechanism of administration may comprise oral consumption, inhalation, topical application, absorption, immersion, injection, and/or other administration methods (such as described elsewhere herein) or a combination thereof. For example, the composition may be administered as a solid, liquid, gas, powder, particle, aerosol, mist, jet, or any mixture thereof. The composition may be in any dosage. The mechanism of administration may be synchronized or tailored to a particular mood or theme of the AR or VR experience. Alternatively or in addition, the mechanism of administration may be timed for purposes of therapy and treatment of psychological and/or physical diseases.

In some cases, a deployment device of the composition that comprises the cannabinoid and/or terpene compound can be operatively coupled to the AR or VR device. Prior to or during the AR or VR experience, the AR or VR device may send one or more control signals to the deployment device based at least in part on the AR or VR experience. The one or more control signals may comprise an instruction to administer such composition to the subject. Examples of the deployment device can include an intravenous infusion pump, aerosol therapy device, inhaler, nebulizer, etc. In some instances, the deployment device may be operatively coupled to a bodily component of a user (e.g., in or near a mouth, in or near a nose, in or near a skin surface, etc.). In some instances, the deployment device may be strategically placed in an AR or VR experience chamber (e.g., at the ceiling, at the walls, at the floor, etc.) with respect to a user interface (e.g., screen, speakers, haptic device, actuator, etc.) and/or the user.

Another aspect of the present disclosure provides a method for subjecting a subject to an interactive experience, comprising (a) administering to the subject a composition comprising a cannabinoid compound. The method may comprise (b) subsequent to and/or during (a), providing an interactive stimulation to the subject, wherein the interactive stimulation comprises a sensory stimulation. The method may comprise (c) detecting a response of the subject to the interactive stimulation. The method may utilize one or more processes or components used in the method for subjecting a subject to an augmented reality (AR) or virtual reality (VR) experience, as provided in the present disclosure.

In some cases, the interactive stimulation may be provided to the subject prior to, during, or subsequent to administration of the cannabinoid compound-containing composition to the subject, in order to (i) improve, enhance, accelerate, and/or prolong the subject's learning abilities, (ii) treat or reduce an effect of the one or more health conditions of the subject, and/or (iii) induce the subject to enter or stay in one or more psychological states (e.g., the flow state) for a longer period of time relative to without such combinatorial therapy. In some cases, the subject can suffer or can be suspected of suffering from one or more health conditions, as provided in the present disclosure.

In some examples, the interactive stimulation of the present disclosure may improve, enhance, accelerate, and/or prolong learning abilities of a pilot (e.g., for flying or landing an airplane), a driver (e.g., for learning to drive a vehicle, or for getting familiarized with a track or course for racing), a medical professional or trainee, such as a surgeon, nurse, or a medical student (e.g., for performing a surgical procedure on a patient), an athlete (e.g., for getting familiarized with a track or course, or for physical therapy), a firefighter or a police (e.g., for training without putting the trainee in real danger), and a soldier (e.g., for a battlefield training, or for post-traumatic stress disorder (PTSD) therapy).

In some cases, the method may comprise (b) subsequent to (a), providing an interactive stimulation to the subject. The method may comprise (b) during (a), providing an interactive stimulation to the subject.

In some cases, the sensory stimulation may comprise a visual stimulation. The visual stimulation may utilize one or more images (e.g., pictures, drawings, etc.) and/or videos. The visual stimulation may utilize at least 1, 2, 3, 4, 5, 6, 7, 8, 9, 10, or more images. The visual stimulation may utilize at most 10, 9, 8, 7, 6, 5, 4, 3, 2, or 1 image(s). The visual stimulation may utilize at least 1, 2, 3, 4, 5, 6, 7, 8, 9, 10, or more videos. The visual stimulation may utilize at most 10, 9, 8, 7, 6, 5, 4, 3, 2, or 1 video(s). The one or more images and/or videos may comprise one or more objects. The one or more objects may be real and/or artificial (e.g., computer generated).

In some cases, the visual stimulation may expose the subject to a light for a predetermined duration, for a predetermined frequency, and/or at a predetermined wavelength or range of wavelengths. In some examples, the visual stimulation may expose the subject to the light for the predetermined duration. The predetermined duration may range between about 1 min to about 10 hours. The predetermined duration may be at least about 1 min, 2 min, 3 min, 4 min, 5 min, 10 min, 20 min, 30 min, 40 min, 50 min, 1 hour, 2 hours, 3 hours, 4 hours, 5 hours, 6 hours, 7 hours, 8 hours, 9 hours, 10 hours, or more. The predetermined duration may be at most about 10 hours, 9 hours, 8 hours, 7 hours, 6 hours, 5 hours, 4 hours, 3 hours, 2 hours, 1 hour, 50 min, 40 min, 30 min, 20 min, 20 min, 5 min, 4 min, 3 min, 2 min, 1 min, or less. The predetermined duration may be assigned by a healthcare practitioner (e.g., a physician, nurse practitioner, nurse, pharmacist, etc.). Alternatively or in addition to, the predetermined duration may be assigned by the user.

In some examples, the visual stimulation may expose the subject to the light for the predetermined frequency. The predetermined frequency may be at least 1 time, 2 times, 3 times, 4 times, 5 times, 6 times, times, 8 times, 9 times, 10 times, 15 times, 20 times, 25 times, 30 times, or more. The predetermined frequency may be at most 30 times, 25 times, 20 times, 15 times, 10 times, 9 times, 8 times, 7 times, 6 times, 5 times, 4 times, 3 times, 2 times, or 1 time. The predetermined frequency of the light may be assigned by a healthcare practitioner (e.g., a physician, nurse practitioner, nurse, pharmacist, etc.). Alternatively or in addition to, the predetermined frequency of the light may be assigned by the user.

In some examples, the visual stimulation may expose the subject to the light at the predetermined wavelength or range of wavelengths (e.g., infrared light, UV light, at least a portion of the visible spectrum, etc.). The predetermined wavelength or range of wavelengths of the light may comprise at least a wavelength or a range of wavelengths from the electromagnetic radiation, as provided in the present disclosure. The predetermined wavelength or range of wavelengths of the light may be assigned by a healthcare practitioner (e.g., a physician, nurse practitioner, nurse, pharmacist, etc.). Alternatively or in addition to, the predetermined frequency of the light may be assigned by the user. In some cases, the light may be provided by at least one light source (e.g., at least 1, 2, 3, 4, 5, or more light sources). The at least one light source may comprise a light amplification by stimulated emission of radiation (LASER or laser) device, a liquid crystal display (LCD) device, a light emitting diode (LED) device, a low pressure sodium lamp, a high-intensity discharge lamp, a fluorescent lamp, an incandescent lamp, etc. The light source may be disposed above, beneath, front, back, and/or one or more sides of the subject during subjecting the subject to the exposure to the light.

In some cases, at least a portion of the body of the subject may be exposed to the light. In some cases, the at least the portion of the body may comprise the head, the shoulder, arm(s), hand(s), torso (e.g., the front and/or back), leg(s), foot/feet, skin, hair, etc. In some cases, the entire body of the subject may be exposed to the light.

In some cases, the sensory stimulation may comprise a temperature change and/or a pressure change. In some cases, the sensory stimulation may be provided in an immersive chamber, as provided in the present disclosure. The immersive chamber may be configured to receive at least a portion of the body of the subject. The immersive chamber may be configured to provide the temperature change and/or the pressure change to the subject for the sensory stimulation. The immersive chamber may comprise a fluid (e.g., liquid, gas, or vapor) configured to receive or be in contact with the at least the portion of the body of the subject. In some examples, the at least the portion of the body may be immersed in the fluid. In some examples, the entire body of the subject may be immersed (submerged) in the fluid.

In some cases, the sensory stimulation may comprise a temperature change. In some examples, at least a portion of the subject may be immersed in or in contact with a fluid, as provided in the present disclosure. In some cases, a temperature of the fluid (e.g., liquid, gas, or vapor) may be controlled to induce the temperature change of the sensory stimulation. The temperature of the liquid may range between about 0° C. to about 50° C. The temperature of the fluid may be at least about 0° C., 1° C., 2° C., 3° C., 4° C., 5° C., 6° C., 7° C., 8° C., 9° C., 10° C., 15° C., 20° C., 25° C., 30° C., 35° C., 40° C., 45° C., 50° C., or more. The temperature of the fluid may be at most about 50° C., 45° C., 40° C., 35° C., 30° C., 25° C., 20° C., 15° C., 10° C., 9° C., 8° C., 7° C., 6° C., ° C., 4° C., ° C., 2° C., 1° C., or less.

In some cases, the sensory stimulation may comprise a pressure change. In some examples, the subject may be in a chamber (e.g., a pressure chamber), as provided in the present disclosure, to experience or be stimulated by the pressure change. The pressure change may comprise an increase and/or decrease in an ambient pressure around the subject at a range between about 1 kPa to about 150 kPa. The pressure change may be an increase and/or decrease in the ambient pressure of at least 1 kPa, 2 kPa, 3 kPa, 4 kPa, 5 kPa, 6 kPa, 7 kPa, 8 kPa, 9 kPa, 10 kPa, 15 kPa, 20 kPa, 25 kPa, 30 kPa, 35 kPa, 40 kPa, 45 kPa, 50 kPa, 60 kPa, 70 kPa, 80 kPa, 90 kPa, 100 kPa, 110 kPa, 120 kPa, 130 kPa, 140 kPa, 150 kPa, or more. The pressure change may be an increase and/or decrease in the ambient pressure of at most 150 kPa, 140 kPa, 130 kPa, 120 kPa, 110 kPa, 100 kPa, 90 kPa, 80 kPa, 70 kPa, 60 kPa, 50 kPa, 45 kPa, 40 kPa, 35 kPa, 30 kPa, 25 kPa, 20 kPa, 15 kPa, 10 kPa, 9 kPa, 8 kPa, 7 kPa, 6 kPa, 5 kPa, 4 kPa, 3 kPa, 2 kPa, 1 kPa, or less.

In some cases, the sensory stimulation may comprise an auditory stimulation. In some cases, the subject may wear an auditory stimulation device (e.g., a headphone, earphone(s), etc.). Alternatively or in addition to, the user may be near or adjacent to one or more auditory stimulation devices (e.g., one or more speakers). Examples of the auditory stimulation can comprise one or more stimuli selected from the group consisting of: sound (e.g., horn, ring, bell, breaking a window, dropping a ball to the ground, grilling a steak, car accident noise, sound of one or more animals, rain, etc.), voice (e.g., speech using one or more languages by one or more speakers), music (e.g., one or more instruments, song with lyrics, song without lyrics, etc.), or combinations thereof.

A frequency of the one or more stimuli of the auditory stimulation may range between about 20 Hz to about 20,000 Hz. The frequency of the one or more stimuli of the auditory stimulation may be at least about 20 Hz, 25 Hz, 30 Hz, 35 Hz, 40 Hz, 45 Hz, 50 Hz, 60 Hz, 70 Hz, 80 Hz, 90 Hz, 100 Hz, 500 Hz, 1,000 Hz, 5,000 Hz, 10,000 Hz, 20,000 Hz, or more. The frequency of the one or more stimuli of the auditory stimulation may be at most about 20,000 Hz, 10,000 Hz, 5,000 Hz, 1,000 Hz, 500 Hz, 100 Hz, 90 Hz, 80 Hz, 70 Hz, 60 Hz, 50 Hz, 45 Hz, 40 Hz, 35 Hz, 30 Hz, 25 Hz, 20 Hz, or less.

In some cases, the sensory stimulation may comprise a haptic stimulation. The term "haptic sensation" or "haptic stimulation," as used interchangeably herein, can refer to a physical sensation (e.g., a touch or tactile sensation exerted on at least a portion (e.g., skin) of the subject). The term "haptic system" or "haptic device," as used interchangeably herein, can refer to a system configured to provide a haptic stimulation (e.g., vibrations, pulses, textures, etc.) on or adjacent to at least a portion of the body of the subject. In some cases, the haptic device may provide the haptic stimulation to the subject (e.g., a user of the haptic device) in response to contact of the subject to the haptic device. In such cases, the haptic device may be a haptic feedback device. In some cases, the haptic device may provide the haptic stimulation to the subject (e.g., a user of the haptic device) in the absence or regardless of any contact of the subject to the haptic device.

In some cases, the haptic device can include one or more actuators (e.g., piezoelectric transducers, electromechanical devices, and/or other vibration inducing devices, etc.). The haptic device can further comprise one or more controllers (e.g., processors, drive electronics, etc.) coupled to the actuator(s) to direct the actuator(s) to induce a selected haptic stimulation into a surface (e.g., the skin of the subject) to which they are attached on or adjacent to, thereby providing a haptic (e.g., tactile) sensation to the subject. In some cases, the haptic device may be worn by the subject. The haptic device may be part of an article of clothing, such as, for example, a hat, helmet, glove(s), shirt, sweater, undergarment(s), pant(s), sock(s), shoe(s), jackets, etc. Alternatively or in addition to, the haptic device may be held by the subject, and examples of such haptic device may include personal devices (e.g., mobile phones, tablet computers, smart watches, smart glasses, etc.).

In some cases, the one or more sensory stimulations (e.g., light, temperature change, pressure change, auditory stimulation, and/or haptic stimulation) may be provided prior to, during, and/or subsequent to the AR or VR experience. In some cases, the one or more sensory stimulations may be provided to the subject as part of a AR or VR experience.

Figure 4A:
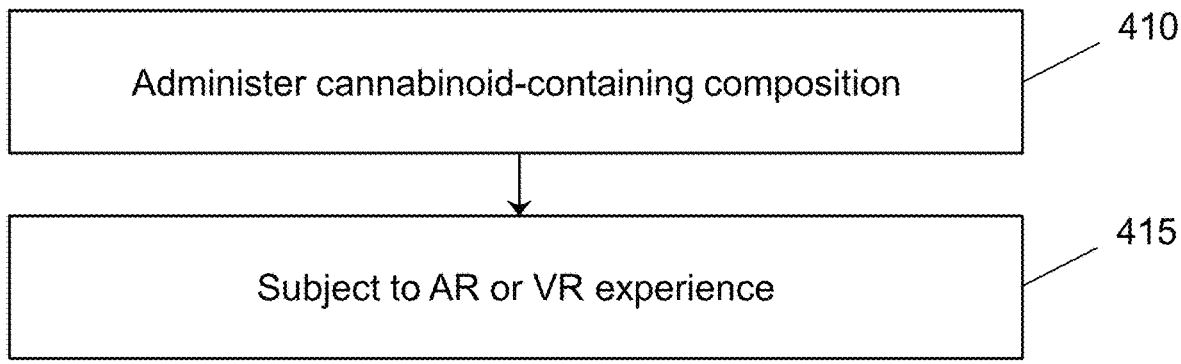
FIGS. 4A-4C show examples of flowcharts of a method for subjecting a subject to AR or VR experience.
Figure 4B:
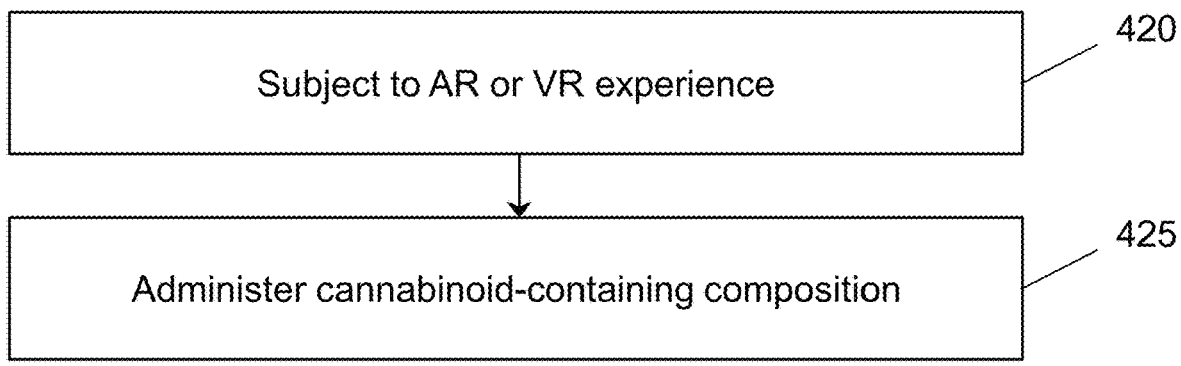
Figure 4C:
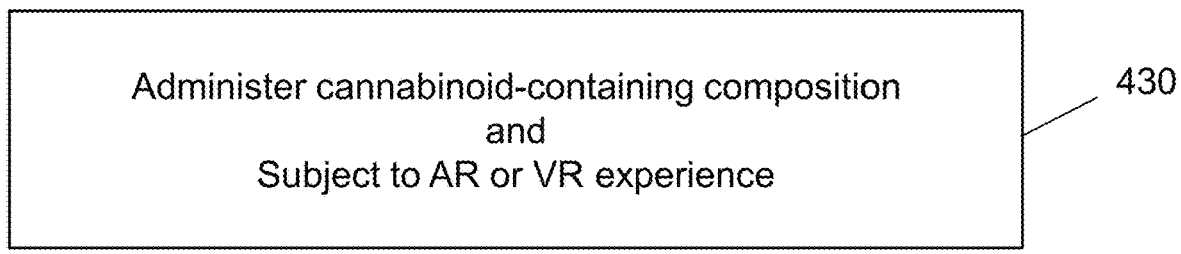

FIGS. 4A-4C show examples of flowcharts of a method for subjecting a subject to AR or VR experience. Referring to FIG. 4A, the method may comprise administering one or more cannabinoid-containing compositions to the subject (process 410), and subsequently subjecting the subject the subject to AR or VR experience (process 415). Referring to FIG. 4B, the method may comprise subjecting the subject to AR or VR experience (process 420), and subsequently administering one or more cannabinoid-containing compositions to the subject (process 425). Referring to FIG. 4C, the method may comprise administering one or more cannabinoid-containing compositions to the subject while subjecting the subject the subject to AR or VR experience (process 430).

FIGS. 5A-5F show examples of flowcharts of a method for subjecting a subject to an interactive experience. The interactive experience may comprise providing neo more sensory simulations of the present disclosure. The one or more sensory stimulations may be provided prior to, during, or subsequent to AR or VR experience. For example, the one or more sensory stimulations may be provided as part of the AR or VR experience. The cannabinoid-containing compositions of the present disclosure may be administered to the subject at any time, such as (i) prior to, during, or subsequent to the provision of the one or more sensory stimulations to the subject, and/or (ii) prior to, during, or subsequent to the AR or VR experience.

Figure 5A:
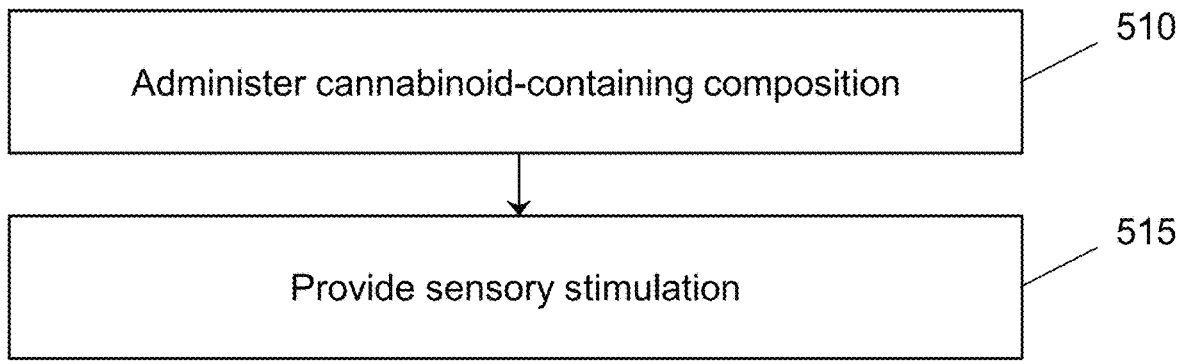
FIGS. 5A-5F show examples of flowcharts of a method for subjecting a subject to an interactive experience.
Figure 5B:
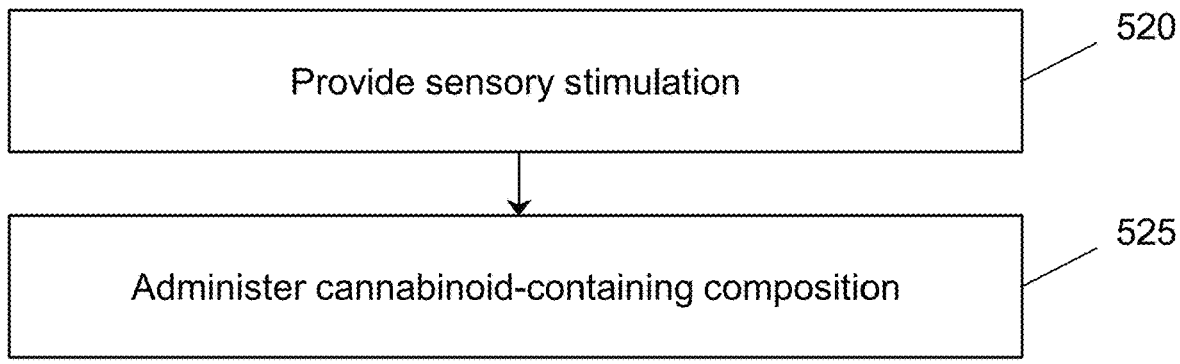

Referring to FIG. 5A, the method may comprise administering one or more cannabinoid-containing compositions to the subject (process 510), and subsequently providing one or more sensory stimulations to the subject (process 515). Referring to FIG. 5B, the method may comprise providing one or more sensory stimulations to the subject (process 520), and subsequently administering one or more cannabinoid-containing compositions to the subject (process 525).

Figure 5C:
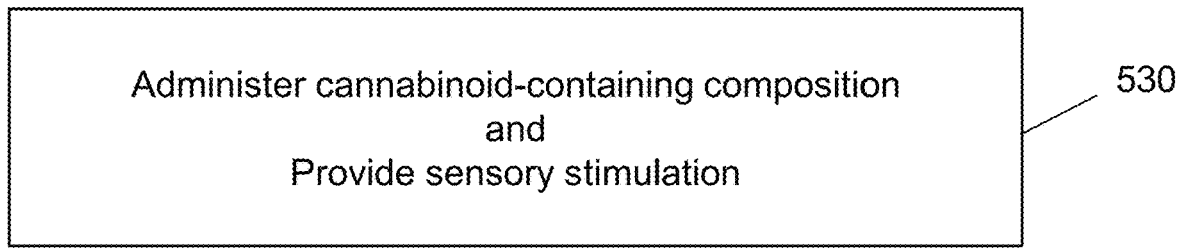

Referring to FIG. 5C, the method may comprise administering one or more cannabinoid-containing compositions to the subject while providing one or more sensory stimulations to the subject (process 530).

Figure 5D:
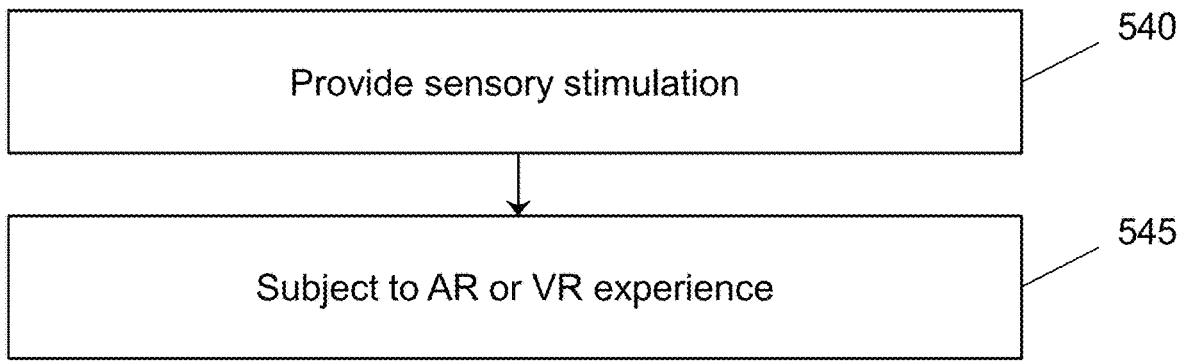
Figure 5E:
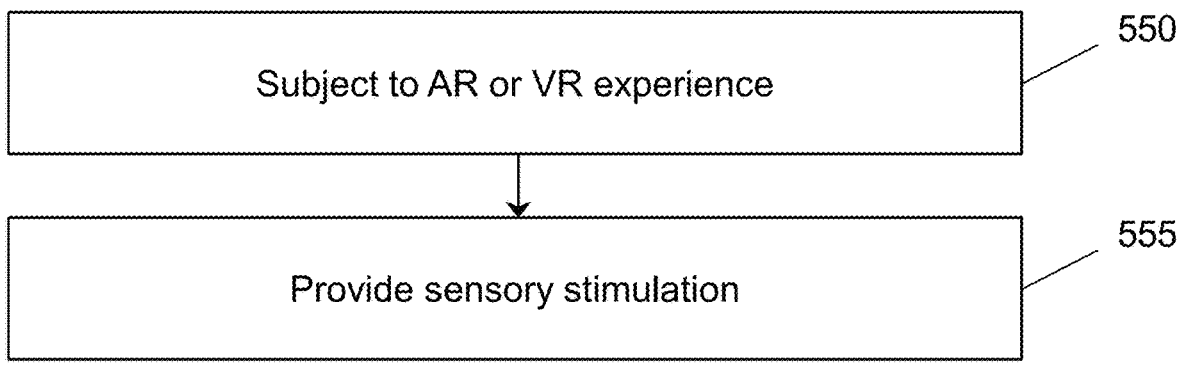
Figure 5F:
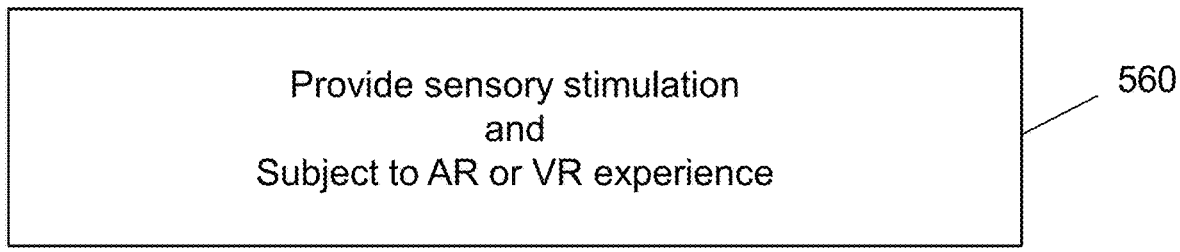

Referring to FIG. 5D, the method may comprise providing one or more sensory stimulations to the subject (process 540), and subsequently subjecting the subject to AR or VR experience (process 545). Referring to FIG. 5E, the method may comprise subjecting the subject to AR or VR experience (process 550), and subsequently providing one or more sensory stimulations to the subject (process 555). Referring to FIG. 5F, the method may comprise providing one or more sensory stimulations to the subject while subjecting the subject to AR or VR experience (process 560).

Compositions

Cannabinoids utilized in the compositions disclosed herein include but are not limited to cannabigerol-type (CBG), cannabigerolic acid (CBGA), cannabigerolic acid monomethylether (CBGAM), cannabigerol monomethyl ether (CBGM), cannabichromene-type (CBC), cannabichromanon (CBCN), cannabichromenic acid (CBCA), cannabichromevarin-type (CBCV), cannabichromevarinic acid (CBCVA), cannabidiol-type (CBD), tetrahydrocannabinol-type (THC), iso-tetrahydrocannabinol-type (iso-THC), cannabinol-type (CBN), cannabinolic acid (CBNA), cannabinol methylether (CBNM), cannabinol-$C_4$ (CBN-$C_4$), cannabinol-$C_2$ (CBN-$C_2$), cannabiorcol (CBN-$C_1$), cannabinodiol (CBND), cannabielsoin-type (CBE), cannabielsoic acid A (CBEA-A), cannabielsoic acid B (CBEA-B), cannabicyclol-type (CBL), cannabicyclolic acid (CBLA), cannabicyclovarin (CBLV), cannabicitran-type (CBT), cannabitriol, cannabitriolvarin (CBTV), ethoxy-cannabitiolvarin (CBTVE), cannabivarin-type (CBV), cannabinodivarin (CBVD), tetrahydrocannabivarin-type (THCV), cannabidivarin-type (CBDV), cannabigerovarin-type (CBGV), cannabigerovarinic acid (CBGVA), cannabifuran (CBF), dehydrocannabifuran (DCBF), and cannabiripsol (CBR) cannabinoids.

Cannabinoids used in compositions of the present disclosure can be derived from various sources, including but not limited to hemp (e.g., hemp stalk, hemp stem, hemp seed), cannabis (e.g., cannabis flower, cannabis leaf, cannabis stalk, cannabis stem, cannabis seed), *Echinacea purpurea, Echinacea angustifolia, Echinacea pallida, Acmella oleracea, Helichrysum umbraculigerum, Radula marginata*, kava, black truffle, *Syzygium aromaticum* (cloves), *Rosmarinus oficinalis*, basil, oregano, black pepper, lavender, true cinnamon, malabathrum, *Cananga odorata, Copaifera* spp., and hops.

Encapsulated cannabinoids can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabinoids can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabinoids can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabinoids can be present in a quantity of from about 1 to about 10 micrograms per microcapsule. Encapsulated cannabinoids can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabinoids can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabinoids can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

Cannabinoids can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabinoids can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabinoids can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabinoids can be present in a product, such as a food product, in a quantity of from about 50 to about 150 milligrams. Cannabinoids can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabinoids can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabinoids can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

The cannabinoids of the compositions disclosed herein can comprise cannabidiol-class compounds, including but not limited to cannabidiol (CBD), cannabidiolic acid (CBDA), cannabidiol monomethylether (CBDM), cannabidiol-$C_4$ (CBD-$C_4$), cannabidivarin (CBDV), cannabidivarinic acid (CBDVA), cannabidiorcol (CBD-$C_1$), and combinations thereof. CBD can comprise delta-1-cannabidiol, delta-2-cannabidiol, delta-3-cannabidiol, delta-3,7-cannabidiol, delta-4-cannabidiol, delta-5-cannabidiol, delta-6-cannabidiol, and combinations thereof.

Encapsulated cannabidiol compounds can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabidiol compounds can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabidiol compounds can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabidiol compounds can be present in a quantity of from about 1 to about 10 micrograms per microcapsule. Encapsulated cannabidiol compounds can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabidiol compounds can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabidiol compounds can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

Cannabidiol compounds can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabidiol compounds can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabidiol compounds can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabidiol compounds can be present in a product, such as a food product, in a quantity of from about 50 to about 150 milligrams. Cannabidiol compounds can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabidiol compounds can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabidiol compounds can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

The compositions of the present disclosure can comprise tetrahydrocannabinol (THC) as a type of cannabinoids. THC can comprise delta-9-THC, delta-8-THC, and combinations thereof. THC can comprise delta-6a,7-tetrahydrocannabinol, delta-7-tetrahydrocannabinol, delta-8-tetrahydrocannabinol, delta-9,11-tetrahydrocannabinol, delta-9-tetrahydrocannabinol, delta-10-tetrahydrocannabinol, delta-6a,10a-tetrahydrocannabinol, and combinations thereof. Delta-9-tetrahydrocannabinol can comprise stereoisomers including (6aR,10aR)-delta-9-tetrahydrocannabinol, (6aS,10aR)-delta-9-tetrahydrocannabinol, (6aS,10aS)-delta-9-tetrahydrocannabinol, (6aR,10aS)-delta-9-tetrahydrocannabinol, and combinations thereof.

In cases where the compositions comprise microcapsules, THC compounds can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated THC compounds can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated THC compounds can be present in a quantity of from about 1 to about 10 micrograms per microcapsule. Encapsulated THC compounds can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated THC compounds can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated THC compounds can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated THC compounds can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

THC compounds can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). THC compounds can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). THC compounds can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). THC compounds can be present in a product, such as a food product, in a quantity of from about 50 to about 150 milligrams. THC compounds can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. THC compounds can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. THC compounds can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

In some cases, a composition of the present disclosure does not contain a psychoactive amount of THC. For example, cannabinoids in compositions of the present disclosure can contain less than 100%, 90%, 80%, 70%, 60%, 50%, 40%, 30%, 20%, 10%, 5%, 1%, 0.7%, 0.5%, 0.3%, or 0.1% THC relative to the total quantity of cannabinoid compounds. In some cases, the ratio of a non-THC cannabinoid (e.g., cannabidiol) to THC in a composition of the present disclosure is greater than or equal to about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, or 100:1. In some cases, compositions of the present disclosure contain less than 0.3% THC.

The compositions of the present disclosure can comprise one or more terpene compounds, including but not limited to terpenoids such as monoterpenoids, sesquiterpenoids, diterpenoids, and triterpenoids. Terpenes can be acyclic, monocyclic, or polycyclic. Terpenes can include but are not limited to myrcene, limonene, linalool, trans-ocimene, cis-ocimene, alpha-pinene, beta-pinene, alpha-humulene (alpha-caryophyllene), beta-caryophyllene, delta-3-carene, trans-gamma-bisabolene, cis-gamma-bisabolene, trans-alpha-farnesene, cis-beta-farnesene, beta-fenchol, beta-phellandrene, guajol, alpha-gualene, alpha-eudesmol, beta-eudesmol, gamma-eudesmol, terpinolene, alpha-selinene, beta-selinene, alpha-terpineol, fenchone, camphene, cis-sabinene hydrate, alpha-trans-bergamotene, alpha-cis-bergamotene, borneol, gamma-curcumene, alpha-thujene, epi-alpha-bisabolol, ipsdienol, alpha-ylangene, beta-elemene, gamma-muurolene, alpha-cadinene, alpha-longipinene, caryophyllene oxide, and combinations thereof.

Encapsulated terpenes can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated terpenes can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated terpenes can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated terpene compounds can be present in a quantity of from about 1 to about 10 micrograms per microcapsule. Encapsulated terpenes can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated terpenes can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated terpenes can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

Terpene compounds can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Terpene compounds can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Terpene compounds can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Terpene compounds can be present in a product, such as a food product, in a quantity of from about 50 to about 150 milligrams. Terpene compounds can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Terpene compounds can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Terpene compounds can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

The compositions of the present disclosure can be enriched in cannabinoids compared to hemp oil. For example, a composition can comprise hemp oil and cannabinoids from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of cannabinoids compared to hemp oil.

The compositions of the present disclosure can be enriched in cannabidiol compounds compared to hemp oil. For example, a composition can comprise hemp oil and cannabidiol compounds from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of cannabidiol compounds compared to hemp oil.

The compositions of the present disclosure can be enriched in THC compounds compared to hemp oil. For example, a composition can comprise hemp oil and THC compounds from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of THC compounds compared to hemp oil.

The compositions of the present disclosure can be enriched in terpenes compared to hemp oil. For example, a composition can comprise hemp oil and terpenes from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of terpenes compared to hemp oil.

Compounds included in the compositions of the present disclosure can be derived from various sources. Compound sources can be natural, such as plant extracts or essential oils. Compounds in the compositions of the present disclosure can be derived from hemp oil, including cannabinoid compounds, THC compounds, and terpene compounds. Compounds in the compositions of the present disclosure can be derived from essential oils, including but not limited to those essential oils discussed further in this disclosure. These compounds can include cannabinoid compounds and terpene compounds. In some cases, all the compounds or ingredients in a composition are natural or naturally-derived. In some cases, all the compounds or ingredients in a composition are vegetarian. In some cases, all the compounds or ingredients in a composition are vegan.

Terpenes and/or essential oils in compositions of the present disclosure can be selected to provide benefits for particular conditions or subjects. Terpenes and/or essential oils can be employed in combination with each other, as well as in combination with cannabinoids, for example to target treatment of particular conditions. For example, terpinolene, terpineol and linalool or lavender, valerian and jasmine essential oils can be combined with cannabinoids or cannabis extract to act as a sleep aid or treat sleep disorders.

Alpha-pinene can be used as an anti-inflammatory, an antiangiogenic, an anti-ulcer agent, and a bronchodilator.

Linalool can be used for reducing anxiety, reducing inflammation (e.g., lung inflammation), to improve Alzheimer's disease or symptoms thereof, as a sedative, an analgesic, an anti-microbial, an antibacterial, and an anti-epileptic.

Myrcene can be used as an antibacterial, a neuroprotective agent, an antinociceptive, an analgesic, and to alleviate neuropathic pain, peptic ulcer disease, and inflammation. Depending on concentration, myrcene can be used as a sedative (e.g., over 0.5% myrcene) or to provide energizing effects (e.g., less than 0.5% myrcene).

Limonene can be used to reduce anxiety and depression, to dissolve cholesterol-containing gallstones, to neutralize gastric acid, support normal peristalsis, relieve heartburn and gastroesophageal reflux, to improve immune function, and as a chemopreventative against cancer.

Ocimene can be used as an antifungal agent, an antitumor agent, and a cyctotoxic agent.

Terpinolene can be used for antioxidant, mood regulation, central nervous system (CNS) regulation, anti-inflammatory, anti-diarrheal, anti-filarial, anti-fungal, antimalarial, anti-amoebic, anti-bacterial, cytotoxic, and anticancer effects.

Terpineol can be used to relax a subject, to aid digestion and improve gastrointestinal disorders, and to relieve influenza, bronchitis, cough, nasal congestion, and sinusitis.

Beta-caryophyllene can be used as an anti-inflammatory agent, an anti-tumor agent, and an analgesic.

Geraniol can be used to reduce or protect against neuropathy, as an antidepressant, to suppress angiogenesis, to improve anti-cancer agent efficacy, to suppress growth of cancer cells (e.g., lung cancer), as a chemopreventive against cancer, to reduce inflammation and apoptosis (e.g., in liver cells), to reduce oxidative stress, as an antioxidant, and as an antimicrobial.

Alpha-humulene can be used as an appetite suppressant, an anti-inflammatory agent, an insect repellant, an antibacterial, an antioxidant, and an allelopathic agent.

Phellandrene can be used as an antidepressant and an antihyperalgesic.

Carene can be used as an antioxidant, an antiproliferative, an antimicrobial, and to reduce excess body fluid production, such as of tears, mucous, or sweat.

Terpinene can be used as an antioxidant, an anti-inflammatory, an antimicrobial, an antiproliferative, to reduce oxidative stress, and to manage diabetes.

Fenchol can be used as an antibacterial agent, an antimycobacterial, an antimicrobial, and an antioxidant.

Borneol can be used to alleviate hyperalgesia, as a TRPA1 inhibitor, an anti-inflammatory agent, and an anti-nociceptive agent.

Bisabolol can be used as an anti-cancer agent, such as to induce apoptosis in leukemia, an anti-tumor agent (e.g., pancreatic cancer), and an antigenotoxicity agent.

Phytol can be used to relax a subject, such as by inhibiting degradation of GABA, as an anxiolytic, to resist menadione-induced oxidative stress, and as an antimicrobial.

Camphene can be used for pain relief, as an antioxidant, to induce apoptosis in cancer cells (e.g., melanoma), an antitumor agent, and an antibacterial.

Sabinene can be used as an antioxidant, an antimicrobial, an anticancer agent (e.g., oral, liver, lung, colon, melanoma, and leukemic cancer), to aid liver function, aid digestion, relieve arthritis, and relieve skin conditions.

Camphor can be used to improve skin healing (e.g., reconstructed human epidermis), as a local anesthetic, a muscle relaxant, an antipathogenic, and an antimicrobial agent.

Isoborneol can be used as an antioxidant, a cytotoxic, a DNA-protective, to inhibit herpes simplex virus type 1, and to inhibit HIV.

Menthol can be used as an analgesic, to desensitize α3β4 nicotinic acetylcholine receptors, as an antinociceptive, and as an anti-inflammatory agent.

Nerolidol can be used as an antifungal agent, an antimicrobial agent, an antioxidant, and an antimalarial agent.

Guaiol can be used as an antimicrobial agent, an antifungal agent, and an antibiotic.

Isopulegol can be used as a gastroprotective agent, an anti-inflammatory agent, to enhance permeability for transdermal administration of compounds, and to reduce the severity of seizures.

Geranyl acetate can be used as an antimicrobial agent, an antibacterial, and an antioxidant.

Cymene can be used as an anti-inflammatory agent, an anti-hyperalgesic, an antioxidant, an anti-diabetic, to aid in weight loss, to aid immune disorders, and to protect against acute lung injury.

Eucalyptol can be used as an antifungal agent, to alleviate inflammation (e.g., lung inflammation), an antioxidant, and an anticancer agent.

Pulegone can be used to enhance skin permeability, as an insecticide, and an antioxidant.

The compositions of the present disclosure can comprise one or more essential oils or essential oil compounds. Essential oils can include, but are not limited to: Linalool; B-Caryophyllene; B-Myrcene; D-Limonene; Humulene; a-Pinene; Ylang Ylang (*Cananga odorata*); Yarrow (*Achillea millefolium*); Violet (*Viola odorata*); Vetiver (*Vetiveria zizanoides*); Vanilla (*Vanilla plantifolia*); Tuberose (*Polianthes tuberosa*); Thyme (*Thymus vulgaris* L.); Tea Tree (*Melaleuca alternifolia*); Tangerine (*Citrus reticulata*); Spruce, Black (*Picea mariana*); Spruce (*Tsuga Canadensis*); Spikenard (*Nardostachys jatamansi*); Spearmint (*Mentha spicata*); Sandalwood (*Santalum spicatum*); Rosewood (*Aniba rosaeodora*); Rosemary Verbenone (*Rosmarinus officinalis*); Rosemary (*Rosmarinus officinalis*); Rose (*Rosa damascena*); Rose Geranium (*Pelargonium roseum*); Ravensara (*Ravensara aromatica*); Plai (*Zingiber cassumunar*) Pine Needle (*Pinus sylvestris* L.); Petitgrain (*Citrus aurantium*); Peppermint (*Mentha piperita*); Pepper, Black (*Piper nigrum* L.); Patchouli (*Pogostemon cablin*); Palo Santo (*Bursera graveolens*); Palmarosa (*Cymbopogon martini*); Osmanthus (*Osmanthus fragrans*); Oregano (*Origanum vulgare*); Orange, Sweet (*Citrus sinensis*); Oak Moss (*Evernia prunastri*); Nutmeg (*Myristica fragrans*) Niaouli (*Melaleuca viridifloria*); Neroli (aka Orange Blossom) (*Citrus aurantium*); Myrtle (*Myrtus communis*); Myrrh (*Commiphora myrrha*); Mimosa (*Acacia decurrens*); Melissa (*Melissa officinalis* L.); Marjoram, Sweet (*Origanum majorana*); Manuka (*Leptospermum scoparium*); Mandarin, Red (*Citrus deliciosa*); Mandarin (*Citrus deliciosa*); Lotus, White (*Nelumbo nucifera*); Lotus, Pink (*Nelumbo nucifera*); Lotus, Blue (*Nelumbo nucifera*); Lime (*Citrus aurantifolia*); Lily (*Lilum aurantum*); Lemongrass (*Cymbopogon citratus*); Lemon (*Citrus limonum*); Lavender (*Lavandula angustifolium*); Lavandin (*Lavandula hybrida* grosso); Kanuka (*Kunzea ericoides*); Juniper Berry (*Juniperus cummunis*); Jasmine (*Jasminum officinale*); Jasmine Abs (*Jasminum sambac*); Helichrysum (*Helichrysum italicum*); Grapefruit, White (*Citrus x paradisi*); Grapefruit, Pink (*Citrus paradisi*); Ginger (*Zingiber officinalis*); Geranium (*Pelargonium graveolens*); Geranium, Bourbon (*Pelargonium graveolens*, 'Herit); Gardenia (*Gardenia jasminoides*); Galbanum (*Ferula galbaniflua*); Frankincense (*Boswellia carterii*); Frangipani (*Plumeria alba*); Fir Needle White (*Abies alba*); Fir Needle Siberia (*Abies siberica*); Fir Needle Canada (*Abies balsamea*); Fennel, Sweet (*Foeniculum vulgare*); Eucalyptus Smithii, Eucalyptus Radiata, Eucalyptus Globulus, Eucalyptus Citriodora, Eucalyptus Blue Mallee (*Eucalyptus polybractea*); Elemi (*Canarium luzonicum*); Dill (*Anethum graveolens*); Cypress (*Cupressus sempervirens*); Cumin (*Cuminum cyminum*); Coriander (*Coriandum sativum*); Cocoa (*Theobroma cacao*); Clove (*Eugenia caryophylatta*); Clary Sage (*Salvia sclarea*); Cistus (aka Labdanum) (*Cistus ladaniferus* L.); Cinnamon (*Cinnamomum zeylanicum*); Chamomile, Roman (*Anthemis nobilis*); Chamomile, Blue (*Matricaria chamomilla*); Celery Seed (*Apium graveolins*); Cedarwood, Western Red (*Thuja plicata*); Cedarwood, Blood (*Juniperus virginiana*); Cedarwood Atlas (*Cedrus atlantica*); Carrot Seed (*Daucus carota*); Cardamon (*Elettaria cardamomum*); Caraway Seed (*Carum carvi*); Cajeput (*Melaleuca cajuputi*); Cade (*Juniperus oxycedrus*); Birch, White (*Betula alba*); Birch, Sweet (*Betula lenta*); Bergamot (*Citrus bergamia*); Bay Laurel (*Laurus nobilis*); Basil (*Ocimum basilicum*); Basil, Holy (*Ocimum sanctum*); Basil (*Ocimum basilicum*); Balsam Poplar (*Populus balsamifera*); Balsam Peru (*Myroxylon balsamum*); Angelica (*Angelica archangelica* L.); and combinations thereof.

The compositions of the present disclosure can comprise one or more additional ingredients, including but not limited to mushrooms or mushroom derivative products (e.g., reishi mushroom, chaga mushroom, maitake mushroom, oyster mushroom, cordyceps), maca (*Lepidium meyenii*), he sho wu (also he show wu or shou wu chih), superfoods or superfood derivative products (e.g., blueberries, acai berries, inca berries, goji berries, camucamu, coconut, lucuma, kale, cacao (e.g., cacao powder, cacao butter), sacha inchi, chia, flax, hemp, amaranth, quinoa, moringa oleifera), and combinations thereof.

Compounds used in compositions of the present disclosure can be extracted by a variety of methods. For example, extraction can be performed by maceration, infusion, decoction, percolation, Soxhlet extraction, pressurized solvent extraction, counter current extraction, ultrasonication, or supercritical fluid (e.g., carbon dioxide) extraction.

In some cases, compounds used in compositions of the present disclosure are extracted via supercritical fluid (e.g., carbon dioxide) extraction. For example, cannabinoid compounds can be extracted from hemp (e.g., hemp stalk and hemp stems) using supercritical carbon dioxide extraction.

The compositions of the present disclosure can comprise pregnenolone, including derivatives thereof. Pregnenolone can help protect a subject from cannabis intoxication, for example from THC. Pregnenolone or derivatives thereof can be formulated to be water soluble. A composition of the present disclosure can comprise between about 1 and 50 milligrams (mg) of pregnenolone or derivatives thereof. For example, a unit dosage of the present disclosure can comprise between about 1 and 50 milligrams (mg) of pregnenolone. Compositions of the present disclosure (e.g., unit dosages) can comprise about 1, 2, 3, 4, 5, 6, 7, 8, 9, 10, 15, 20, 25, 30, 35, 40, 45, or 50 mg of pregnenolone. Compositions of the present disclosure (e.g., unit dosages) can comprise at least about 1, 2, 3, 4, 5, 6, 7, 8, 9, 10, 15, 20, 25, 30, 35, 40, 45, or 50 mg of pregnenolone. Compositions of the present disclosure (e.g., unit dosages) can comprise at most about 1, 2, 3, 4, 5, 6, 7, 8, 9, 10, 15, 20, 25, 30, 35, 40, 45, or 50 mg of pregnenolone. Compositions comprising pregnenolone can be used in combination with any other compounds, ingredients, or formulations described herein, including esters, cyclodextrin complexes, microcapsules (e.g., sodium alginate microcapsules), immediate release formulations, delayed or extended release formulations, transbuccal formulations, and sublingual formulations.

Compositions of the present disclosure can be used to treat various diseases or conditions in subjects (e.g., humans, mammals, vertebrates), including but not limited to ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions (e.g., psoriasis, dermatitis, allergic inflammation, chronic pruritus), sleep disorders (e.g., sleep-wake disorders, apnea), spinal cord injury, stress, stroke, and traumatic brain injury (TBI).

Encapsulation and Delivery

The compositions of the present disclosure can comprise microcapsules. Microcapsules can comprise components discussed in this disclosure, such as cannabinoid compounds, terpene compounds, cannabidiol, THC, and others, in microencapsulated form. In some cases, compositions can be encapsulated without the use of liposomes. In some cases, compositions can be encapsulated without the use of micelles. In some cases, compositions can be encapsulated without the use of liposomes or micelles. Compounds of the composition can exist within a microcapsule in forms including but not limited to liquid, gel, semi-solid, and solid. Microcapsules of compositions disclosed herein can further be processed into forms including but not limited to solids, powders, liquids, suspensions, gels, tablets, foods, lotions, cosmetics, and other forms discussed in this disclosure.

Microencapsulation can be performed with a microencapsulation device, including microfluidic droplet generation or encapsulation devices. An example of a microencapsulation device is described, for example, in U.S. Pat. No. 7,482,152, incorporated here by reference in its entirety. Microfluidic droplets or emulsions can be generated by flow of a fluid to be encapsulated with an immiscible carrier fluid. For example, an oil fluid to be encapsulated can be flowed with an aqueous carrier fluid, or an aqueous fluid to be encapsulated can be flowed with an oil carrier fluid. Air can also be used as a fluid. Microfluidic droplet generators useful for microencapsulation include those employing co-flowing streams, cross-flowing streams (e.g., flow of streams at a T-junction), flow focusing, flow through perforated plates, and flow through nozzles. Droplet size can be controlled by parameters including device geometry, relative flow rates of the fluid streams, and operating pressure.

Microencapsulation can be performed at a range of operating parameters, such as different flow rates or pressures. Microencapsulation can be conducted at a pressure of at least about 10 pounds per square inch (psi), 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, 1000 psi, 2000 psi, 3000 psi, 4000 psi, 5000 psi, 6000 psi, 7000 psi, 8000 psi, 9000 psi, 10000 psi, 15000 psi, 20000 psi, 25000 psi, 30000 psi, 35000 psi, 40000 psi, 45000 psi, 50000 psi, or more. Microencapsulation can be conducted at a pressure of at most about 10 pounds per square inch (psi), 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, 1000 psi, 2000 psi, 3000 psi, 4000 psi, 5000 psi, 6000 psi, 7000 psi, 8000 psi, 9000 psi, 10000 psi, 15000 psi, 20000 psi, 25000 psi, 30000 psi, 35000 psi, 40000 psi, 45000 psi, or 50000 psi. Microencapsulation can be conducted at a pressure of about 10 pounds per square inch (psi), 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, 1000 psi, 2000 psi, 3000 psi, 4000 psi, 5000 psi, 6000 psi, 7000 psi, 8000 psi, 9000 psi, 10000 psi, 15000 psi, 20000 psi, 25000 psi, 30000 psi, 35000 psi, 40000 psi, 45000 psi, 50000 psi, or more. Microencapsulation can be conducted at a flow rate of at least about 1 milliliter per minute (mL/min), 2 mL/min 3 mL/min, 4 mL/min, 5 mL/min, 6 mL/min, 7 mL/min, 8 mL/min, 9 mL/min, 10 mL/min, 20 mL/min, 30 mL/min, 40 mL/min, 50 mL/min, 60 mL/min, 70 mL/min, 80 mL/min, 90 mL/min, 100 mL/min, 110 mL/min, 120 mL/min, 130 mL/min, 140 mL/min, 150 mL/min, 160 mL/min, 170 mL/min, 180 mL/min, 190 mL/min, 200 mL/min, 210 mL/min, 220 mL/min, 230 mL/min, 240 mL/min, 250 mL/min, 260 mL/min, 270 mL/min, 280 mL/min, 290 mL/min, 300 mL/min, 310 mL/min, 320 mL/min, 330 mL/min, 340 mL/min, 350 mL/min, 360 mL/min, 370 mL/min, 380 mL/min, 390 mL/min, 400 mL/min, 410 mL/min, 420 mL/min, 430 mL/min, 440 mL/min, 450 mL/min, 460 mL/min, 470 mL/min, 480 mL/min, 490 mL/min, 500 mL/min, or more. Microencapsulation can be conducted at a flow rate of at most about 1 milliliter per minute (mL/min), 2 mL/min 3 mL/min, 4 mL/min, 5 mL/min, 6 mL/min, 7 mL/min, 8 mL/min, 9 mL/min, 10 mL/min, 20 mL/min, 30 mL/min, 40 mL/min, 50 mL/min, 60 mL/min, 70 mL/min, 80 mL/min, 90 mL/min, 100 mL/min, 110 mL/min, 120 mL/min, 130 mL/min, 140 mL/min, 150 mL/min, 160 mL/min, 170 mL/min, 180 mL/min, 190 mL/min, 200 mL/min, 210 mL/min, 220 mL/min, 230 mL/min, 240 mL/min, 250 mL/min, 260 mL/min, 270 mL/min, 280 mL/min, 290 mL/min, 300 mL/min, 310 mL/min, 320 mL/min, 330 mL/min, 340 mL/min, 350 mL/min, 360 mL/min, 370 mL/min, 380 mL/min, 390 mL/min, 400 mL/min, 410 mL/min, 420 mL/min, 430 mL/min, 440 mL/min, 450 mL/min, 460 mL/min, 470 mL/min, 480 mL/min, 490 mL/min, or 500 mL/min. Microencapsulation can be conducted at a flow rate of about 1 milliliter per minute (mL/min), 2 mL/min 3 mL/min, 4 mL/min, 5 mL/min, 6 mL/min, 7 mL/min, 8 mL/min, 9 mL/min, 10 mL/min, 20 mL/min, 30 mL/min, 40 mL/min, 50 mL/min, 60 mL/min, 70 mL/min, 80 mL/min, 90 mL/min, 100 mL/min, 110 mL/min, 120 mL/min, 130 mL/min, 140 mL/min, 150 mL/min, 160 mL/min, 170 mL/min, 180 mL/min, 190 mL/min, 200 mL/min, 210 mL/min, 220 mL/min, 230 mL/min, 240 mL/min, 250 mL/min, 260 mL/min, 270 mL/min, 280 mL/min, 290 mL/min, 300 mL/min, 310 mL/min, 320 mL/min, 330 mL/min, 340 mL/min, 350 mL/min, 360 mL/min, 370 mL/min, 380 mL/min, 390 mL/min, 400 mL/min, 410 mL/min, 420 mL/min, 430 mL/min, 440 mL/min, 450 mL/min, 460 mL/min, 470 mL/min, 480 mL/min, 490 mL/min, 500 mL/min, or more.

Droplet generators can employ multiple parallel droplet generation operations in parallel. For example, a droplet generator (e.g., a plate, a device with channels) can employ at least 1, 2, 3, 4, 5, 6, 7, 8, 9, 10, 15, 20, 25, 30, 35, 40, 45, 50, 55, 60, 65, 70, 75, 80, 85, 90, 95, 100, or more droplet generating features (e.g., holes, channels, nozzles). A droplet generator can employ at most 1, 2, 3, 4, 5, 6, 7, 8, 9, 10, 15, 20, 25, 30, 35, 40, 45, 50, 55, 60, 65, 70, 75, 80, 85, 90, 95, or 100 droplet generating features. A droplet generator can employ about 1, 2, 3, 4, 5, 6, 7, 8, 9, 10, 15, 20, 25, 30, 35, 40, 45, 50, 55, 60, 65, 70, 75, 80, 85, 90, 95, 100, or more droplet generating features.

Microencapsulation can be performed via an emulsification process. For example, compositions can be emulsified in a mixer, such as an agitator, impeller, centrifugal mixer, or high-shear mixer. High-shear mixers can include batch high-shear mixers and inline high-shear mixers (e.g., rotor-stator mixers). Emulsification can also be conducted without a mixer, by combining fluids thermodynamically favored to form an emulsion, optionally with the aid of one or more emulsifiers or surfactants.

Microencapsulation processes can be conducted with the aid of one or more emulsifiers or surfactants. Emulsifiers and surfactants can include but are not limited to saponins (e.g., quillaja tree extract such as Q-NATURALE®, yucca extract), lecithin, soy lecithin, mustard seed hull extract, sodium stearoyl lactylate, polysorbate 20, and combinations thereof.

Microcapsules can comprise one or more stabilizers or gelling agents, which can be used to stabilize a microcapsule or emulsion. Stabilizers or gelling agents can include but are not limited to alginate (also algin or alginic acid) and agar. Alginate can be used in a variety of forms, including but not limited to inorganic salts such as sodium alginate, potassium alginate, calcium alginate, and combinations thereof. Alginate can be derived from sources such as seaweed (e.g., *Macrocystis pyrifera, Ascophyllum nodosum, Laminaria* spp.) or bacteria (e.g., *Pseudomonas* spp., *Azotobacter* spp.). Cross-linking agents or solutions, such as calcium chloride, can be used to stabilize or gel microcapsules.

Microcapsules can be characterized by a size (e.g., a diameter). The microcapsule size can be about 0.154 micrometers. The microcapsule size can be less than or equal to about 0.154 micrometers. The microcapsule size can be greater than or equal to about 0.154 micrometers. The microcapsule size can be about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, or 500 micrometers. The microcapsule size can be less than or equal to about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, or 500 micrometers. The microcapsule size can be greater than or equal to about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, or 500 micrometers. The microcapsule size can be from about 0.1 to about 0.2 micrometers. The microcapsule size can be from about 0.05 to about 0.25 micrometers. The microcapsule size can be from about 0.05 to about 0.55 micrometers. The microcapsule size can be from about 0.05 to about 1 micrometers. The size distribution in a population of microcapsules can be homogeneous or substantially homogeneous. For example, a population of microcapsules can be characterized by dispersity, or polydispersity index (PDI), of less than or equal to about 20, 19, 18, 17, 16, 16, 15, 14, 13, 12, 11, 10, 9, 8, 7, 6, 5, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.45, 1.40, 1.35, 1.30, 1.25, 1.20, 1.15, 1.14, 1.13, 1.12, 1.11, 1.10, 1.09, 1.08, 1.07, 1.06, 1.05, 1.04, 1.03, 1.02, 1.01, or 1.00.

The compositions of the present disclosure can be provided as a dry powder. For example, an oil-based composition (e.g., hemp oil) can be combined with a drying or powdering agent, such as cyclodextrin. In some cases, a powder composition can be provided on its own. In other cases, a powder composition can be provided in another product, such as a food product, cosmetic product, or other products and compositions such as those disclosed herein.

The compositions of the present disclosure can be provided in any suitable form, including but not limited to a liquid form, a gel form, a semi-liquid (e.g., a liquid, such as a viscous liquid, containing some solid) form, a semi-solid (a solid containing some liquid) form, or a solid form. Compositions can be provided in, for example, a tablet form, a capsule form, a food form a chewable form, a non-chewable form, a transbuccal form, a sublingual form, a slow-release form, a non-slow-release form, a sustained release form, or a non-sustained-release form.

The compositions of the present disclosure can be administered in any oral dosage form, including liquid dosage forms (e.g., a suspension or slurry), and oral solid dosage forms (e.g., a tablet or bulk powder). Tablets can include tablets, caplets, capsules, including soft gelatin capsules, and lozenges. Tablets can further comprise suitable binders, lubricants, diluents, disintegrating agents, colorants, flavoring agents, flow-inducing agents, and melting agents.

The compositions of the present disclosure can be administered using a variety of different mechanisms. The composition may be nebulized, delivered in an aerosolized an aerosol spray preparation from a pressurized pack, or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

The compositions of the present disclosure can be administered as a dry powder. For example, an oil-based composition (e.g., hemp oil) can be combined with a drying or powdering agent, such as cyclodextrin. In some cases, a powder composition can be provided on its own. In other cases, a powder composition can be provided in another product or composition, such as a food product or composition, cosmetic product, or other products and compositions such as those disclosed herein.

The compositions of the present disclosure can be administered in any suitable form, including but not limited to a liquid form, a gel form, a semi-liquid (e.g., a liquid, such as a viscous liquid, containing some solid) form, a semi-solid (a solid containing some liquid) form, or a solid form. Compositions can be provided in, for example, a tablet form, a capsule form, a food form a chewable form, a non-chewable form, a transbuccal form, a sublingual form, a slow-release form, a non-slow-release form, a sustained release form, or a non-sustained-release form.

The compositions of the present disclosure for inhalation or insufflation can include solutions and suspensions in pharmaceutically acceptable, aqueous or organic solvents, or mixtures thereof, and powders. The liquid or solid compositions may contain suitable excipients as set out above. Preferably the compositions of the present invention are administered by the oral, intranasal or respiratory route for local or systemic effect. Compositions in acceptable solvents may be nebulized by use of inert gases. Nebulized solutions may be inhaled directly from a nebulizing device or a nebulizing device may be attached to a face mask, tent or intermittent positive pressure breathing machine. Solution, suspension or powder compositions may be administered orally or nasally from devices that deliver the formulation in an appropriate manner.

The compositions of the present disclosure can be injected into a bodily part of a subject (e.g., a vein, a marrow, etc. of a patient). Examples of the injection method may include, but are not limited to, intradermal, subcutaneous, intramuscular, intravenous, intraosseous, intraperitoneal, intrathecal, epidural, intracardiac, intraarticular, intracavernous, intravitreal, and/or transdermal.

The compositions of the present disclosure can be administered transdermally, such as via a patch. The compositions of the present disclosure can be administered intravenously. The compositions of the present disclosure can be administered topically. The compositions of the present disclosure can be administered via exposure to an aqueous solution, such as a subject immersing in a float tank. The compositions of the present disclosure can be formulated as a bath salt or liquid bath product, which can be dissolved or dispersed in water (e.g., a bath) for skin exposure, for example by immersion of the subject.

The compositions of the present disclosure can be provided as cosmetics or personal care products, such as soaps (e.g., solid, bar, liquid, or foaming), hand sanitizer, lotions, massage oils masks, makeup, moisturizers, sunscreen, toothpaste, mouth wash, or throat spray. Use of cannabinoids in such applications can provide benefits including reduction of inflammation in a subject.

The compositions of the present disclosure can be provided as a food composition in combination with a food carrier, including but not limited to food bars (e.g., granola bars, protein bars, candy bars), cereal products (e.g., oatmeal, breakfast cereals, granola), bakery products (e.g., bread, donuts, crackers, bagels, pastries, cakes), dairy products (e.g., milk, yogurt, cheese), beverages (e.g., milk-based beverages, sports drinks, fruit juices, teas, soft drinks, alcoholic beverages, bottled waters), beverage mixes, pastas, grains (e.g., rice, corn, oats, rye, wheat, flour), egg products, snacks (e.g., candy, chips, gum, gummies, lozenges, mints, chocolate), meats, fruits, vegetables or combinations thereof. Food compositions can comprise solid foods. Food compositions can comprise semi-solid foods. Food compositions can comprise liquid foods. A composition in a liquid form may be formulated from a dry mix, such as a dry beverage mix or a powder. A dry mix may be suitable in terms of transportation, storage, or shelf life. The composition can be formulated from the dry mix in any suitable manner, such as by adding a suitable liquid (e.g., water, milk, fruit juice, tea, or alcohol).

A food composition or food product can comprise a food bar, including but not limited to granola bars, protein bars, candy bars, and energy bars. A food composition or food product can comprise a cereal product, including but not limited to oatmeal, flour (e.g., wheat flour, rice flour, corn flour, barley flour), breakfast cereal, granola, bread, pasta, rice cakes, and popcorn. A food composition or food product can comprise a bakery product, including but not limited to bread, pastries, brownies, cakes, pies, donuts, crackers, and muffins. A food composition or food product can comprise a dairy product, including but not limited to milk, fermented milk, curd, whey, yogurt, cream, cheese, butter, clarified butter, ghee, and ice cream. A food composition or food product can comprise a nut butter or seed butter, including but not limited to peanut butter, almond butter, cashew butter, hazelnut butter, macadamia nut butter, pecan butter, pistachio butter, walnut butter, pumpkin seed butter, sesame seed butter, soybean butter, and sunflower seed butter. A food composition or food product can comprise an oil (e.g., a cooking oil), including but not limited to olive oil, coconut oil, vegetable oil, canola oil, corn oil, peanut oil, sunflower seed oil, almond oil, avocado oil, rice bran oil, cottonseed oil, flaxseed oil, linseed oil, grape seed oil, hemp oil, mustard oil, macadamia oil, palm oil, tea seed oil, walnut oil, margarine, lard, butter, clarified butter, ghee, or tallow. A food composition or food product can comprise sports food products such as energy gels, sports drinks, energy powders, energy bars, energy shots, protein powders, and protein drinks (e.g., protein shakes). A food composition or food product can comprise a beverage, including but not limited to water, electrolyte drinks, soda, coconut water, tea (e.g., Jun tea, black tea, green tea, white tea, herbal tea), coffee, a soft drink, an alcoholic beverage (e.g., cocktail, liquor, spirits, beer, wine, malt beverage), water, juice (e.g., apple juice, orange juice, tomato juice, vegetable juice, cranberry juice), a sports drink, electrolyte-enriched water, vitamin-enhanced water, a hangover-recovery drink, milk (e.g., dairy-based milk, coconut milk, almond milk, soy milk, hemp milk, rice milk, oat milk, cashew milk, hazelnut milk), and yogurt. A food composition or food product can comprise a fungus or fermented food or drink, including but not limited to kifir (kefir), jun, amasi, amazake, appam, ayran, doogh, bagoong, brem, cheonggukjang, chicha, kombucha, fermented bean curd, kimchi, lassi, miso, poi, yakult, and yogurt.

Compositions of the present disclosure can comprise pet or other animal products, such as animal food (e.g., dog food, cat food), treats, and nutritional supplements (e.g., liquids, sprays, or powders for application to food or water). These compositions can be formulated for or administered to domestic or pet animals (e.g., dogs, cats, small mammals, birds), livestock and other farm animals (e.g., cows, pigs, horses, sheep, goats), zoo animals, or any other vertebrates. Compositions for administration to animals can be formulated with microencapsulated cannabinoid-rich oil or non-encapsulated cannabinoid-rich oil, alone or in combination with essential oils, terpenes, and other components described herein. Compositions for administration to animals can be mixed into feed or water, prepared for spraying application (e.g., mixed in glycerin), for intravenous administration (e.g., in a syringe or an IV bag), in salves, vitamins, liquid vitamin pumps, treats, or other forms.

The compositions of the present disclosure can comprise an additional agent or agents, whether active or passive. Examples of such an agent include a sweetening agent, a flavoring agent, a coloring agent, a filling agent, a binding agent, a lubricating agent, an excipient, a preservative, or a manufacturing agent. Additional pharmaceutically acceptable excipients (in the case of pharmaceuticals) or other additives (for non-pharmaceutical applications) can be added to the composition. For example, if desired, any generally accepted soluble or insoluble inert pharmaceutical filler (diluent) material can be included in the final product (e.g., a solid dosage form). Such inert pharmaceutical filler can comprise a monosaccharide, a disaccharide, a polyhydric alcohol, inorganic phosphates, sulfates or carbonates, and combinations thereof. Examples of suitable inert pharmaceutical fillers include sucrose, dextrose, lactose, xylitol, fructose, sorbitol, calcium phosphate, calcium sulfate, calcium carbonate, microcrystalline cellulose, and combinations thereof. An effective amount of any generally accepted pharmaceutical lubricant, such as calcium or magnesium soaps, can be added.

The compositions of the present disclosure can be administered to a subject.

Compositions can be administered in a variety of ways, including but not limited to oral and topical administration.

Administering the compositions of the present disclosure to a subject can provide one or more beneficial effects. Beneficial effects can include but are not limited to pain relief, reduced bacterial growth, reduced blood sugar levels, improved blood lipid and cholesterol profiles, increased fat burning, reduced appetite, stimulated appetite, reduced vomiting or nausea, reduced seizures or convulsions, antifungal effects, reduced inflammation, reduced arthritis (e.g., rheumatoid arthritis), reduced insomnia or aided sleep, reduced arterial blockage, inhibited cancer cell growth, improved psoriasis, tranquilizing effects, antispasmodic effects, reduced anxiety, bone growth promotion, reduced intestinal contractions, and nervous system protection.

Any of the subject compositions can be provided in a unit dosage form. A unit dosage is an amount of a compound, such as a cannabinoid compound delivered alone or in combination with other components, which is to be administered to a subject at or about one time point. Other components which can be included with a unit dosage include but are not limited to cosmetics, food carriers, food bars, baked goods, dairy products, oils, beverages, solid dosages (e.g., tablets), or liquid dosages. A unit dosage of a cannabinoid compound can be about 10, 20, 30, 40, 50, 60, 70, 80, 90, 100, 125, 150, 175, 200, 250, 300, 350, 400, 450, 500, 600, 700, 800, 900, 1000 or more milligrams (mg). A unit dosage of a cannabinoid compound can be at least about 10, 20, 30, 40, 50, 60, 70, 80, 90, 100, 125, 150, 175, 200, 250, 300, 350, 400, 450, 500, 600, 700, 800, 900, 1000 or more milligrams (mg). A unit dosage of a cannabinoid compound can be at most about 10, 20, 30, 40, 50, 60, 70, 80, 90, 100, 125, 150, 175, 200, 250, 300, 350, 400, 450, 500, 600, 700, 800, 900, 1000 or more milligrams (mg). A unit dosage can be an hourly dosage. A unit dosage can be a daily dosage. A unit dosage can provide about 1/24, 1/12, 1/8, 1/6, 1/4, 1/3, 1/2, or all of a daily dosage of one or more cannabinoids for a subject. A unit dosage can take the form of a tablet, gel, liquid, food product, food bar, container of liquid of defined volume, or other forms described herein, packaged for one-time consumption or administration.

The compositions described herein can provide several advantages, including but not limited to increased shelf stability, increased bioavailability, increased bioactivity, and delayed release. The compositions described herein, when administered to a subject, can have various release profiles, half-lives, and metabolic characteristics. The subject compositions can comprise a plurality of microcapsules, wherein an individual microcapsule in the plurality is characterized by exhibiting at least one of: (a) a sigmoidal release profile of the at least one cannabinoid compound; (b) a plasma half-life of the at least one cannabinoid compound greater than twice that of the at least one cannabinoid compound in non-encapsulated form; (c) a first pass metabolism of the at least one cannabinoid compound reduced by at least 50% compared to the at least one cannabinoid compound in non-encapsulated form; d) a rate of excretion of the at least one cannabinoid compound from a subject's body reduced by at least 20% compared to the at least one cannabinoid compound in non-encapsulated form; or (e) a degradation rate at an ambient temperature of at least 20° C. of the at least one cannabinoid compound of less than about 50% of a degradation rate of the at least one cannabinoid compound in non-encapsulated form.

The compositions described herein can have a shelf half-life of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 240, 270, 300, 330, or 360 days. In some cases, the compositions described herein can have a shelf half-life of at least about 1, 2, 3, 4, or 5 years. Compositions in microencapsulated form can be characterized by a cannabinoid degradation rate at an ambient temperature of at least 20° C. of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than the degradation rate of a non-encapsulated cannabinoid composition.

Cannabinoid compositions in microencapsulated form can be characterized by a plasma half-life in a subject of at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, or 5.0 times that of a non-encapsulated cannabinoid composition. Plasma half-life of a composition can be determined experimentally by administering the composition to a subject, taking plasma samples from a subject at multiple time points, and measuring the concentration of the compound or compounds of interest in those plasma samples. The concentration of the compound or compounds of interest will reach a peak value in the plasma, then fall as the compound or compounds are metabolized, degraded, or cleared from the blood stream. The plasma half-life is the time for the plasma concentration value to be halved.

The cannabinoid release profile can be sigmoidal (e.g., having an 'S' shape curve, such as a logistic function). The cannabinoid release profile can be non-sigmoidal. The cannabinoid release profile can be linear. The cannabinoid release profile can be non-linear. The cannabinoid release profile can be instant release. The cannabinoid release profile can be non-instant release. The cannabinoid release profile can be delayed release. The cannabinoid release profile can be constant or sustained release. The cannabinoid release profile can be non-constant or non-sustained release.

Tablets can be formulated in sustained release format. Methods of making sustained release tablets are known in the art; see, for example, U.S. Patent Publication No. 2006/0051416 and U.S. Patent Publication No. 2007/0065512. Gradual-release tablets are known in the art; examples of such tablets are set forth in U.S. Pat. No. 3,456,049, for example. A slow- or sustained-release form may delay disintegration or absorption of the composition or one or more components thereof.

In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 1 hour of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 2 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 3 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 4 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 5 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 6 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 7 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 8 hours of administration to a subject.

A release profile is the relationship between time and the amount of a compound released into a subject or the concentration of the compound within the subject (e.g., within the plasma). Release profiles can be measured in a similar manner to plasma half-life. A composition can be administered to a subject, and samples (e.g., plasma samples or blood samples) can be taken from the subject at multiple time points. The concentration of the compound or compounds of interest can be measured in those samples, and a release profile can be plotted.

Compounds taken up into a subject via the gastrointestinal system can be transported to the liver before entering general circulation. Compounds susceptible to metabolic degradation in the liver can have their activities substantially reduced by the first-pass metabolism through the liver. Encapsulation (e.g., microencapsulation) of compounds can reduce first-pass metabolism of the compounds in the liver. Compositions in microencapsulated form can be characterized by a first pass cannabinoid metabolism in a subject of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than that of a non-encapsulated cannabinoid composition. Compositions in microencapsulated form can be characterized by a cannabinoid excretion rate from a subject of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than that of a non-encapsulated cannabinoid composition.

The compositions described herein, when administered to a subject, can have improved bioavailability, bioactivity, or both. Bioavailability is the fraction of an administered dosage of unchanged compound that reaches systemic circulation. Cannabinoid compositions in microencapsulated form can be characterized by a bioavailability in a subject of at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, or 10.0 times that of a non-encapsulated cannabinoid composition. Cannabinoid compositions in microencapsulated form can be characterized by a bioavailability in a subject of at least 5%, 10%, 15%, 20%, 25%, 30%, 35%, 40%, 45%, 50%, 55%, 60%, 65%, 70%, 75%, 80%, 85%, 90%, 95%, 96%, 97%,%, 98%, 99%, or 100%. Bioactivity, or biological activity, is the activity exerted by the active ingredient or ingredients in a composition. Cannabinoid compositions in microencapsulated form can be characterized by a bioactivity in a subject of at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, or 10.0 times that of a non-encapsulated cannabinoid composition.

Subjects of the present disclosure can include humans and other animals, such as pets (e.g., dogs, cats, birds, small mammals, snakes) and livestock or farm animals (e.g., cows, pigs, horses, sheep, chickens). Compositions of the present disclosure can be useful for veterinary applications.

Non-limiting examples of a cell (e.g., a cell of a subject) include, but are not limited to, lymphoid cells, such as B cell, T cell (Cytotoxic T cell, Natural Killer T cell, Regulatory T cell, T helper cell), Natural killer cell, cytokine induced killer (CIK) cells, myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula densa cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme—rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Leydig cell of testes, Theca interna cell of ovarian follicle, Corpus luteum cell of ruptured ovarian follicle, Granulosa lutein cells, Theca lutein cells, Juxtaglomerular cell (renin secretion), Macula densa cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

The compositions described herein can be administered to a subject by a drug delivery machine. In some examples, the composition may be operatively coupled to an infusion pump. The infusion pump may be configured for administration (e.g., epidural administration) of at least a portion of the composition to the subject via, e.g., intravenous infusion. The drug delivery machine may be programmable (e.g., by a prescriber of the composition, such as a physician) to control dosage regimen and duration of the administration of the composition to the subject. The drug delivery machine may be controlled by the subject. In an example, the subject may be allowed to initiate and control dosage regimen and duration of the administration of the composition via the drug delivery machine for self-administration. Alternatively, the subject may not or need to control the drug delivery machine for self-administration.

The drug delivery machine may be configured to administer a second agent to the subject. Examples of the second agent may include, but are not limited to, drug therapy (e.g., analgesia), chemotherapy (e.g., for cancer), cell therapy (e.g., stem cell therapy), and gene therapy (e.g., gene knockdown via ribonucleic acid interference (RNAi)). The second agent may be administered to the subject prior to, concurrent with, and/or subsequent to the administration of the composition of the present disclosure (e.g., a composition comprising a cannabinoid compound). In some examples, the drug delivery machine may be configured to mix the second agent with the composition of the present disclosure prior to administration to the subject. In other examples, the composition of the present disclosure and the second agent may be administered to the subject separately.

The drug delivery machine may be operatively in communication (e.g., via Radio-Frequency Identification (RFID), Near-Field Communication (NFC), Bluetooth, Wireless Fidelity (Wi-Fi), etc.) with an AR or VR device of the present disclosure. The drug delivery machine and the AR or VR device may be programmable to coordinate (i) administration of any subject composition of the present disclosure to a subject and (ii) subjecting the subject to an AR or VR experience using an AR or VR device. The AR or VR device may be configured to provide (i) a visual stimulation, (ii) an auditory stimulation, and/or (iii) a haptic stimulation to the subject.

The drug delivery machine may be operatively in communication (e.g., via RFID, NFC, Wi-Fi, etc.) with one or more sensory stimulation devices to provide an interaction experience to a subject in conjunction with administration of a composition comprising a cannabinoid compound to the subject. Examples of the one or more sensory stimulation devices may include, but are not limited to (i) a temperature controller configured to provide a temperature change as a sensory stimulation to a subject, (ii) a pressure controller configured to provide a pressure change as a sensory stimulation to a subject, and (iii) a scent controller to provide a scent change as a sensory stimulation to a subject.

Computer Systems

The present disclosure provides computer systems that are programmed to implement methods of the disclosure. Computer systems of the present disclosure may be used to provide an AR or VR experience to a user via an AR or VR device and/or administer and/or an interactive stimulation to a user.

Figure 6:
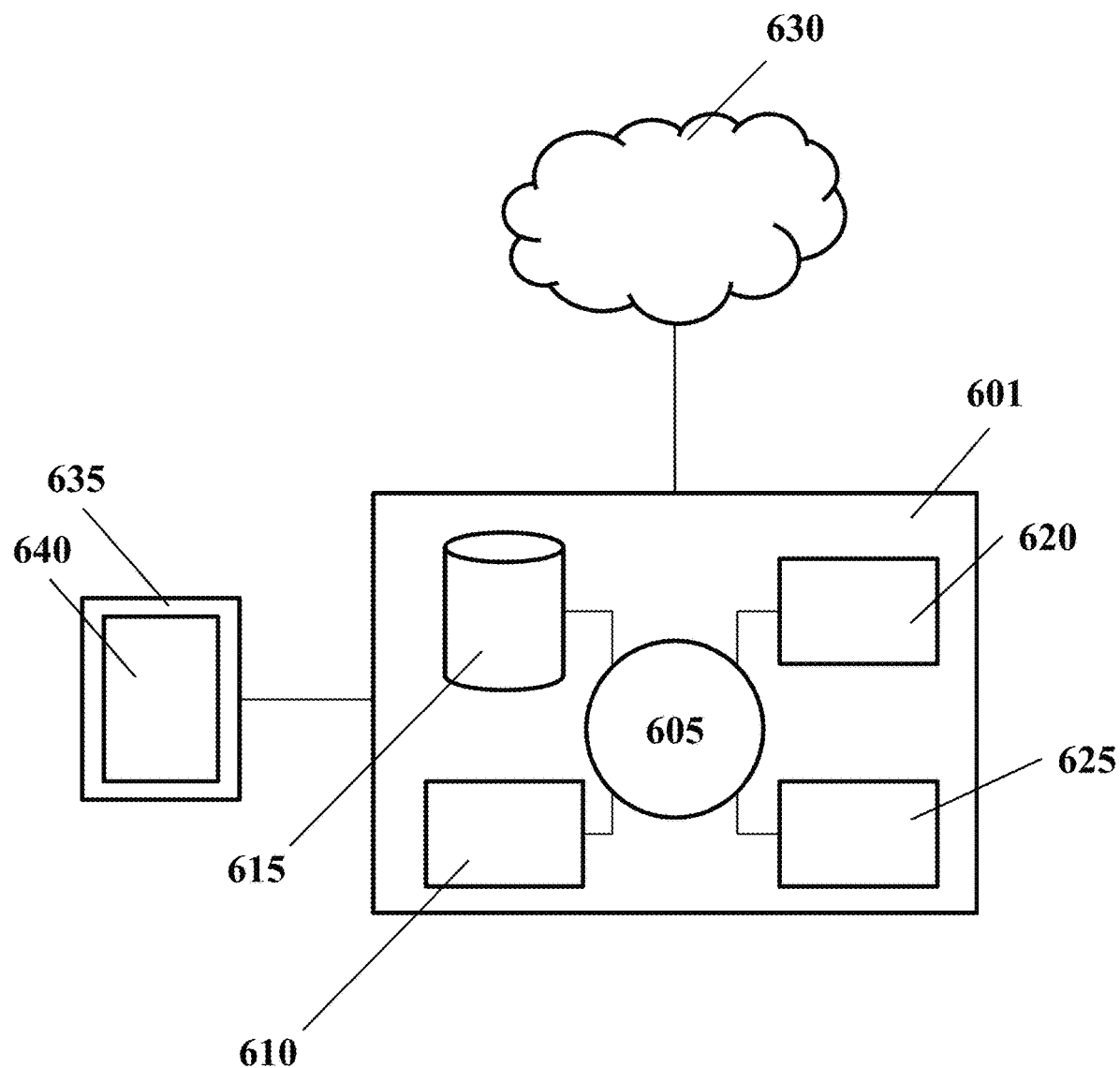
FIG. 6 shows a computer system that is programmed or otherwise configured to implement methods provided herein.

FIG. 6 shows a computer system 601 that is programmed or otherwise configured to communicate with and regulate various aspects of any one of the methods of the present disclosure. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data (i.e., a database). The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databas(es), etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and IR data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for, e.g., (i) activating or deactivating an AR or VR device, (ii) activating or deactivating a drug delivery machine, and/or (iii) activating or deactivating one or more sensory stimulation devices of the present disclosure. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, distinguish or differentiate one or more profiles (e.g., features, such as, for example, dimension(s), volume, shape, or pattern) of a film of the viscous liquid on or adjacent to the build surface based on a feedback from the sensor(s).

EXAMPLES

Provided are examples of cannabinoid compositions for administration or use in conjunction with a VR or AR experience. The cannabinoid compositions may be administered to a subject at any time with respect to the VR or AR experience, such as prior to, during, or subsequent to the VR or AR experience.

Example 1—Microencapsulation of Cannabinoids

A hemp oil composition is produced, comprising cannabinoids including cannabidiol. Additional essential oils are added to the composition. Alginate (e.g., sodium alginate) and quillaja tree extract are added to the composition. The composition is microencapsulated via a microfluidic nozzle device. Calcium chloride is used to cross-link the microcapsules. The microcapsules are packaged in a suspension, transported, and sold.

Example 2—Administration of Cannabinoid Composition to a Subject

A cannabinoid composition, such as the microencapsulated cannabinoid composition described in Example 1, is administered to a subject suffering from a cannabinoid deficiency related condition. The level of cannabinoids in the subject increases, and the condition is improved.

Example 3—Cannabidiol-Rich Hemp and Coconut Oil Product

Hempseed oil is enriched in cannabidiol compounds by addition of hemp stalk and stem extract containing 10% to 40% cannabidiol compounds by weight. The enriched hempseed oil is blended into coconut oil to produce a final composition of about 100 milligrams of cannabidiol compounds in 8 fluid ounces of coconut oil. The coconut oil product is then used to produce consumer products such as moisturizers, lotions, cooking oils, smoothies, spreads, and other food products.

Example 4—Cannabidiolic Acid-Rich Hemp and Coconut Oil Product

Hempseed oil is enriched in cannabidiolic acid by addition of hemp stalk and stem extract containing 10% to 40% cannabidiolic acid by weight. The enriched hempseed oil is blended into coconut oil to produce a final composition of about 100 milligrams of cannabidiolic acid in 8 fluid ounces of coconut oil. The coconut oil product is then used to produce consumer products such as moisturizers, lotions, cooking oils, smoothies, spreads, and other food products.

Example 5—Cannabidiol-Rich Hot Chocolate Mix

Hempseed oil is enriched in cannabidiol compounds by addition of hemp stalk and stem extract containing 10% to 40% cannabidiol compounds. Hempseed oil rich in cannabidiol compounds is then combined with cyclodextrin (e.g., certified organic cyclodextrin) to form a dry powder. The hemp oil powder is mixed with powdered cacao, cacao butter mix, sweeteners, and optionally superfood products such as reishi mushroom powder, chaga mushroom powder, maca, or he shou wu. The mixture is packaged and sold as a chocolate beverage mix (e.g., hot chocolate mix).

Example 6—Production and Packaging of Cannabinoid-Rich Product

A standardized supercritical carbon dioxide extract of hemp stalk and stem is extracted. The extract (e.g., a paste) is blended into hemp seed oil. The blend of hemp extract and hemp oil is prepared with a THC content below 0.3%, and with CBD content of about 10-40% by weight. The hemp extract and hemp oil blend is further blended into coconut oil to provide about 100 mg of CBD per 8 ounce of coconut oil (about 423 milligrams per liter). The coconut oil blend with CBD is packaged (e.g., in a jar) and sold to a consumer.

Example 7—Administration of Pregnenolone Composition to a Subject

A cannabinoid and pregnenolone composition, such as the microencapsulated cannabinoid composition described in Example 1 further comprising pregnenolone (e.g., 1-50 mg of pregnenolone), is administered to a subject suffering from cannabinoid intoxication or addiction. The subject is protected from CB1 receptor overactivation, and the condition is improved.

Example 8—Preparation of Microencapsulated Composition

Formulations comprising quillaja extract (e.g., Q Natural), hemp oil, water, and optionally sodium alginate were prepared using a microfluidic fluid processor (e.g., Microfluidizer from Microfluidics/IDEX Corporation). Formulations were prepared as described in Table 1. Test 1 was prepared with 60 g of quillaja extract (e.g., Q Natural), 80 g of hemp oil, and 100 g of water, at an operating pressure of 30,000 psi in the microfluidic fluid processor. Test 2 was prepared with 10 g of quillaja extract (e.g., Q Natural), 15 g of hemp oil, 198 g of water, and 2 g of sodium alginate, at an operating pressure of 30,000 psi in the microfluidic fluid processor.

After processing in the microfluidic fluid processor, particle size distribution was analyzed using a laser diffraction particle size analyzer (e.g., Horiba LA950). Optical microscope images were also taken.

Three passes each of Test 1 and Test 2 were conducted, and the tenth percentile (D10), fiftieth percentile (D50), and ninetieth percentile (D90) particle sizes are reported in Table 1. Particle sizes were also analyzed for an unprocessed solution (Test 1, Pass 0).

TABLE 1

Formulation and size distribution information for microencapsulated compositions.

| Test | Pass # | Pressure | Q Natural | Hemp Oil | Water | Sodium alginate | D10 (μm) | D50 (μm) | D90 (μm) |
|---|---|---|---|---|---|---|---|---|---|
| 1 | 0 | 30,000 psi | 60 g | 80 g | 100 g | — | 1.9737 | 7.117 | 35.703 |
|   | 1 |   |   |   |   | — | 0.0768 | 0.1296 | 0.2881 |
|   | 2 |   |   |   |   | — | 0.0697 | 0.1096 | 0.1791 |
|   | 3 |   |   |   |   | — | 0.0929 | 0.1405 | 0.2202 |
| 2 | 1 | 30,000 psi | 10 g | 15 g | 198 g | 2 g | 0.1171 | 0.1965 | 2.0719 |
|   | 2 |   |   |   |   |   | 0.0688 | 0.1097 | 0.2209 |
|   | 3 |   |   |   |   |   | 0.099 | 0.1583 | 1.3443 |

Figure 1B:
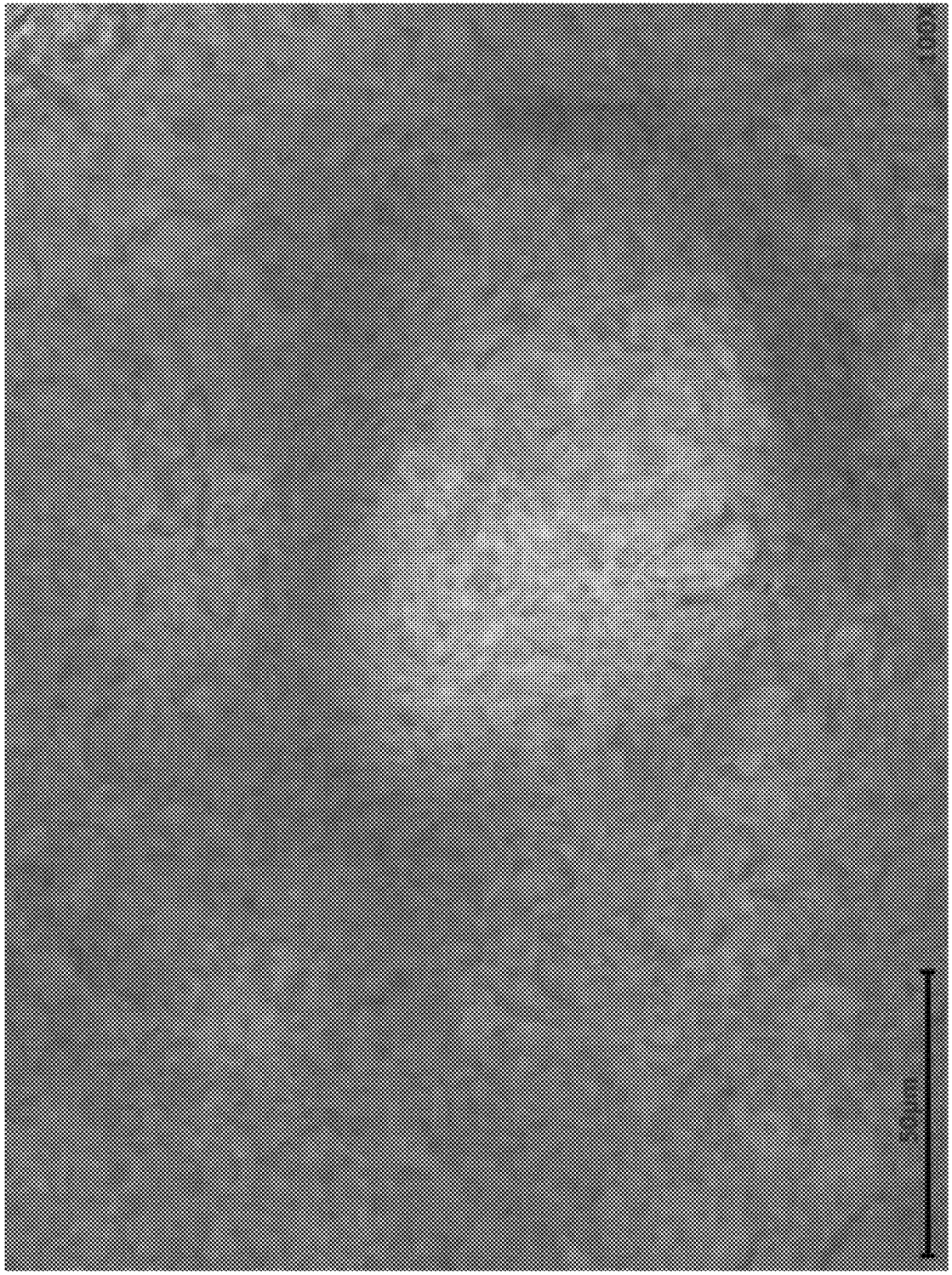
FIG. 1B shows an example of a microscope image of an unprocessed composition of quillaja extract, hemp oil, and water at 1000× magnification.

FIG. 1A shows a 400× magnification micrograph image of an unprocessed quillaja extract, hemp oil, and water composition (Test 1, Pass 0), with a 50 μm scale bar. FIG. 1B shows a 1000× magnification micrograph image of an unprocessed quillaja extract, hemp oil, and water composition (Test 1, Pass 0), with a 50 μm scale bar.

Figure 2A:
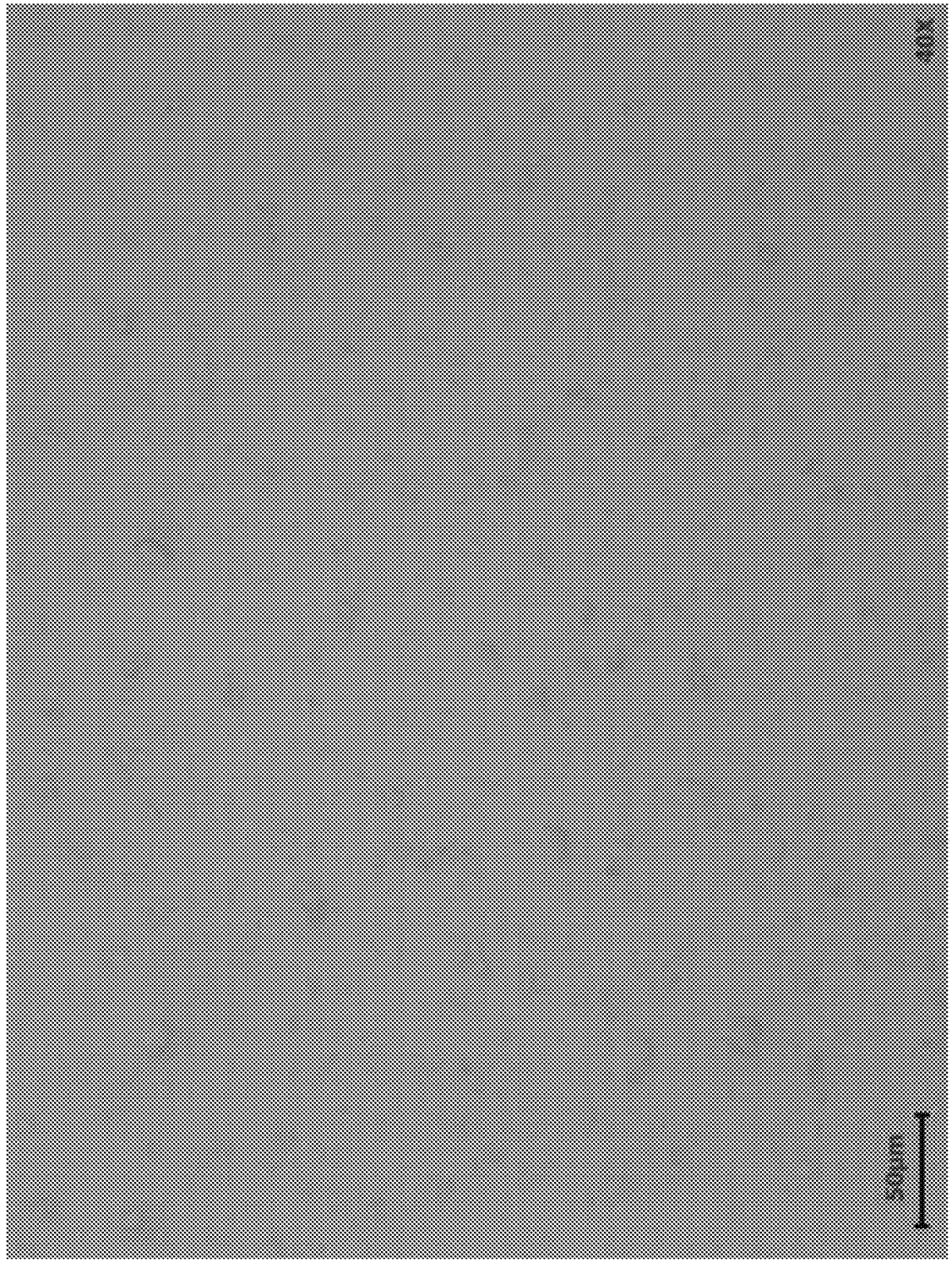
FIG. 2A shows an example of a microscope image of a microfluidic processed composition of quillaja extract, hemp oil, and water at 400× magnification.
Figure 2B:
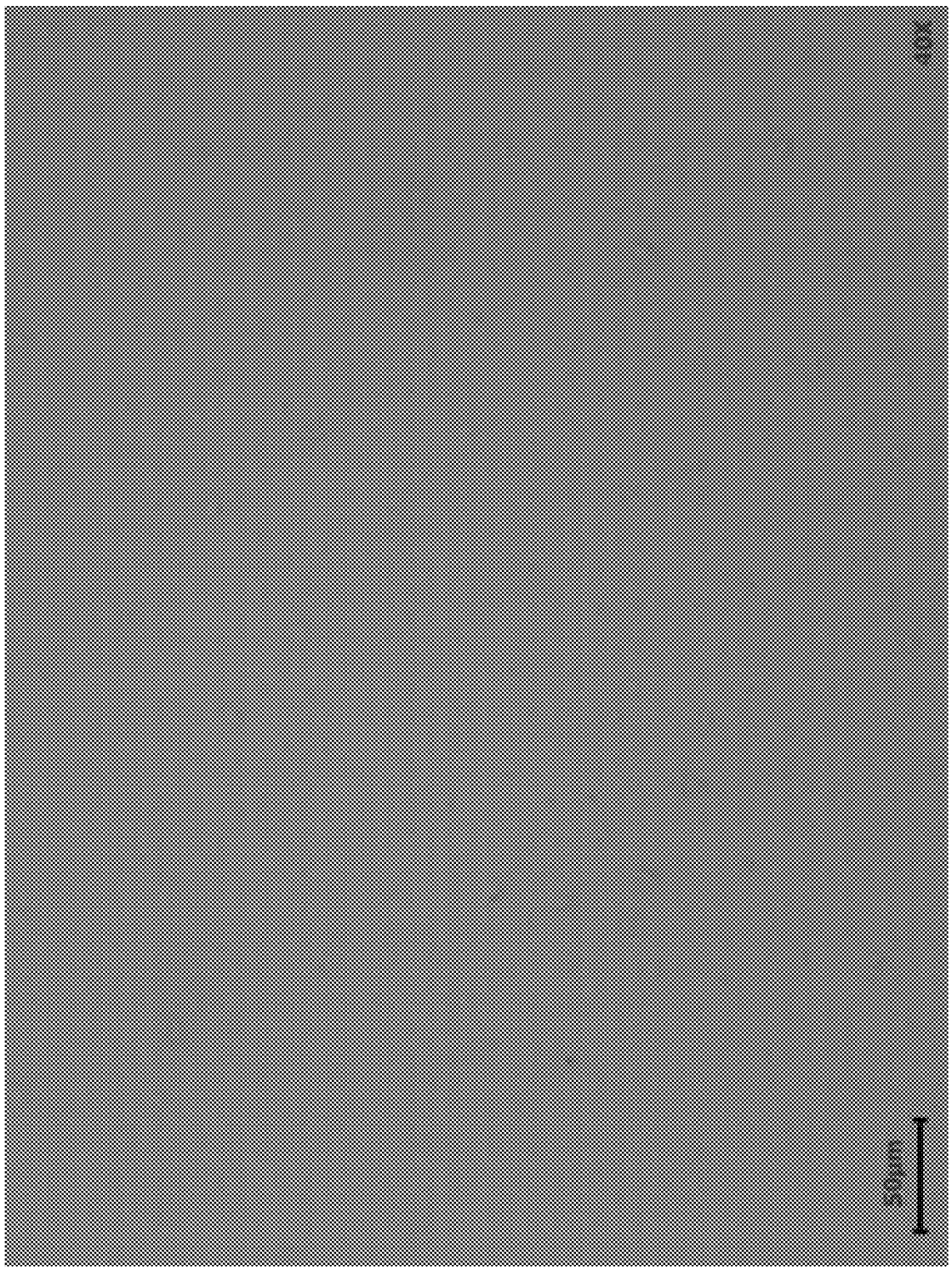
FIG. 2B shows an example of a microscope image of a microfluidic processed composition of quillaja extract, hemp oil, and water at 400× magnification.
Figure 2C:
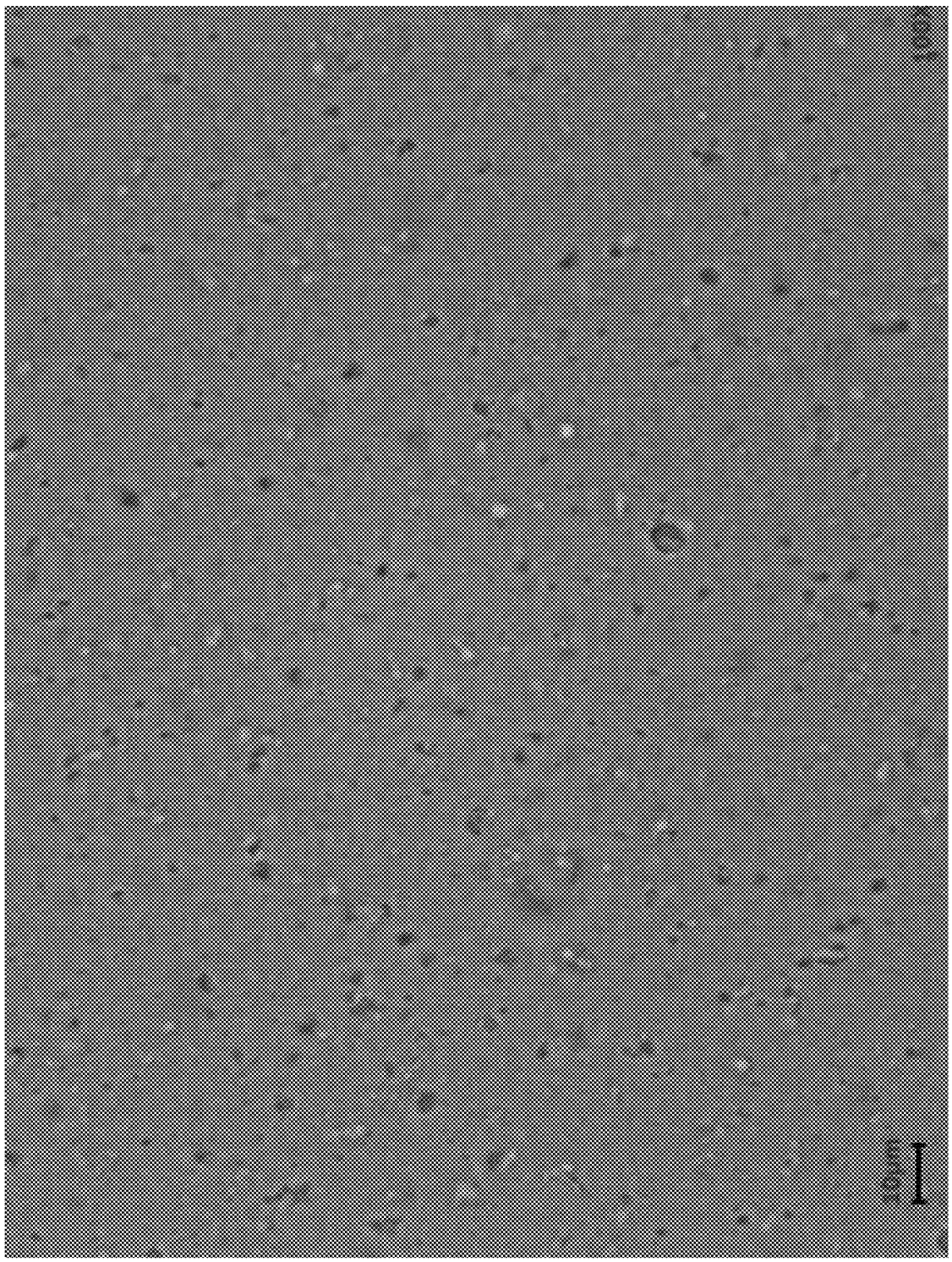
FIG. 2C shows an example of a microscope image of a microfluidic processed composition of quillaja extract, hemp oil, and water at 1000× magnification.
Figure 2D:
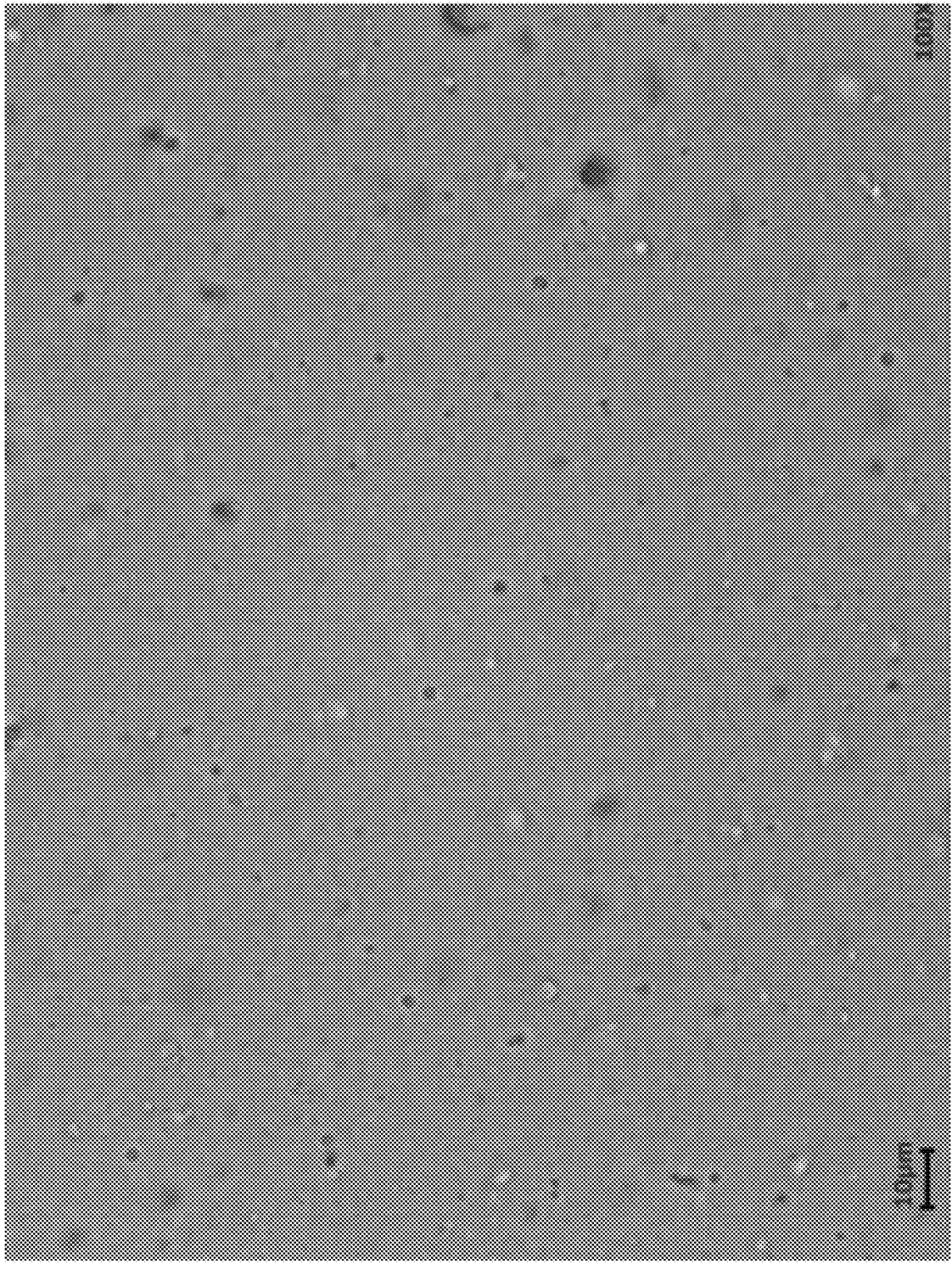
FIG. 2D shows an example of a microscope image of a microfluidic processed composition of quillaja extract, hemp oil, and water at 1000× magnification.

FIG. 2A shows a 400× magnification micrograph image of a quillaja extract, hemp oil, and water composition (Test 1, Pass 1), with a 50 μm scale bar. FIG. 2B shows a 400× magnification micrograph image of a quillaja extract, hemp oil, and water composition (Test 1, Pass 2), with a 50 μm scale bar. FIG. 2C shows a 1000× magnification micrograph image of a quillaja extract, hemp oil, and water composition (Test 1, Pass 2), with a 10 μm scale bar. FIG. 2D shows a 1000× magnification micrograph image of a quillaja extract, hemp oil, and water composition (Test 1, Pass 3), with a 10 μm scale bar.

Figure 3A:
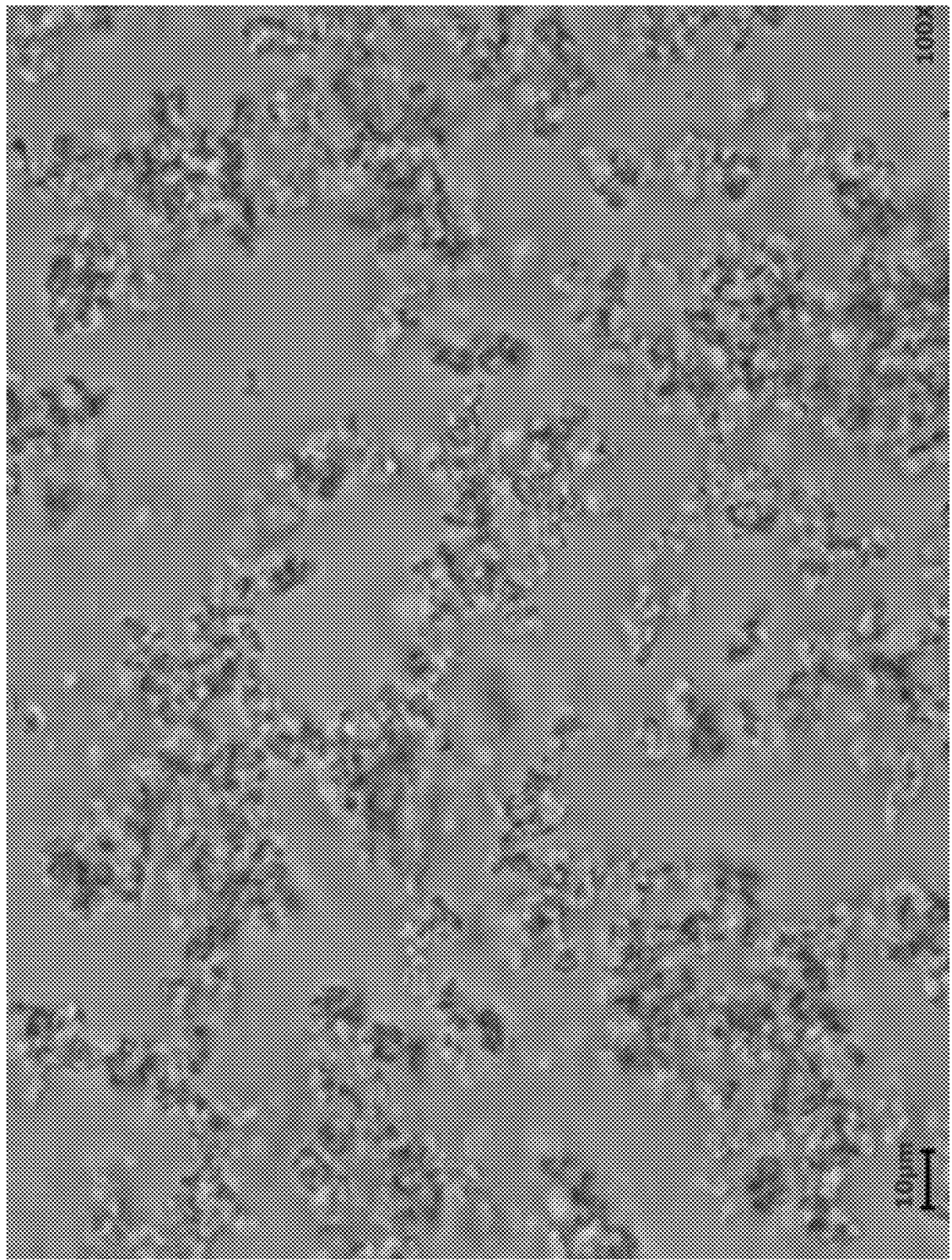
FIG. 3A shows an example of a microscope image of a microfluidic processed composition of quillaja extract, hemp oil, water, and sodium alginate at 1000× magnification.
Figure 3B:
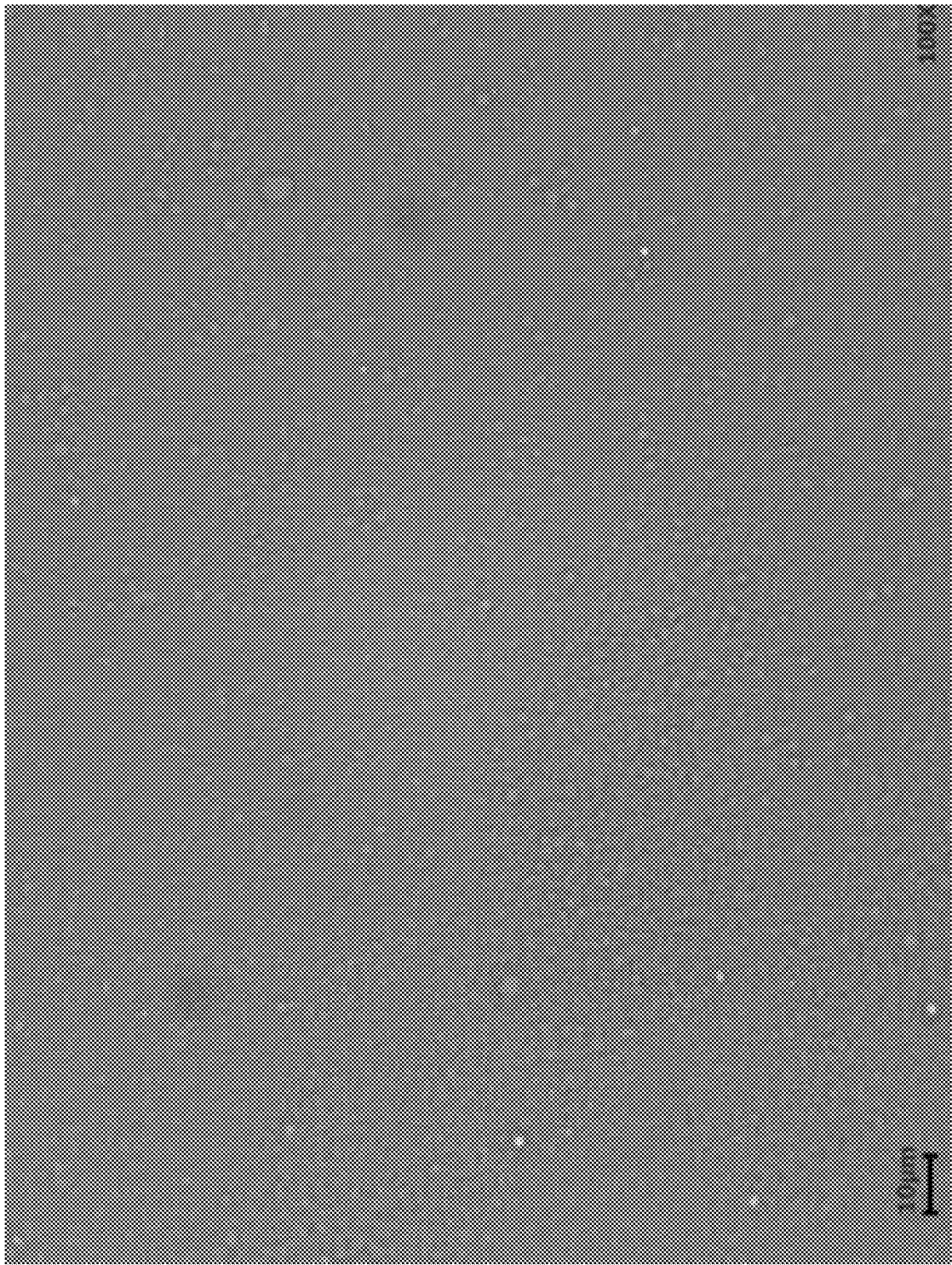
FIG. 3B shows an example of a microscope image of a microfluidic processed composition of quillaja extract, hemp oil, water, and sodium alginate at 1000× magnification.
Figure 3C:
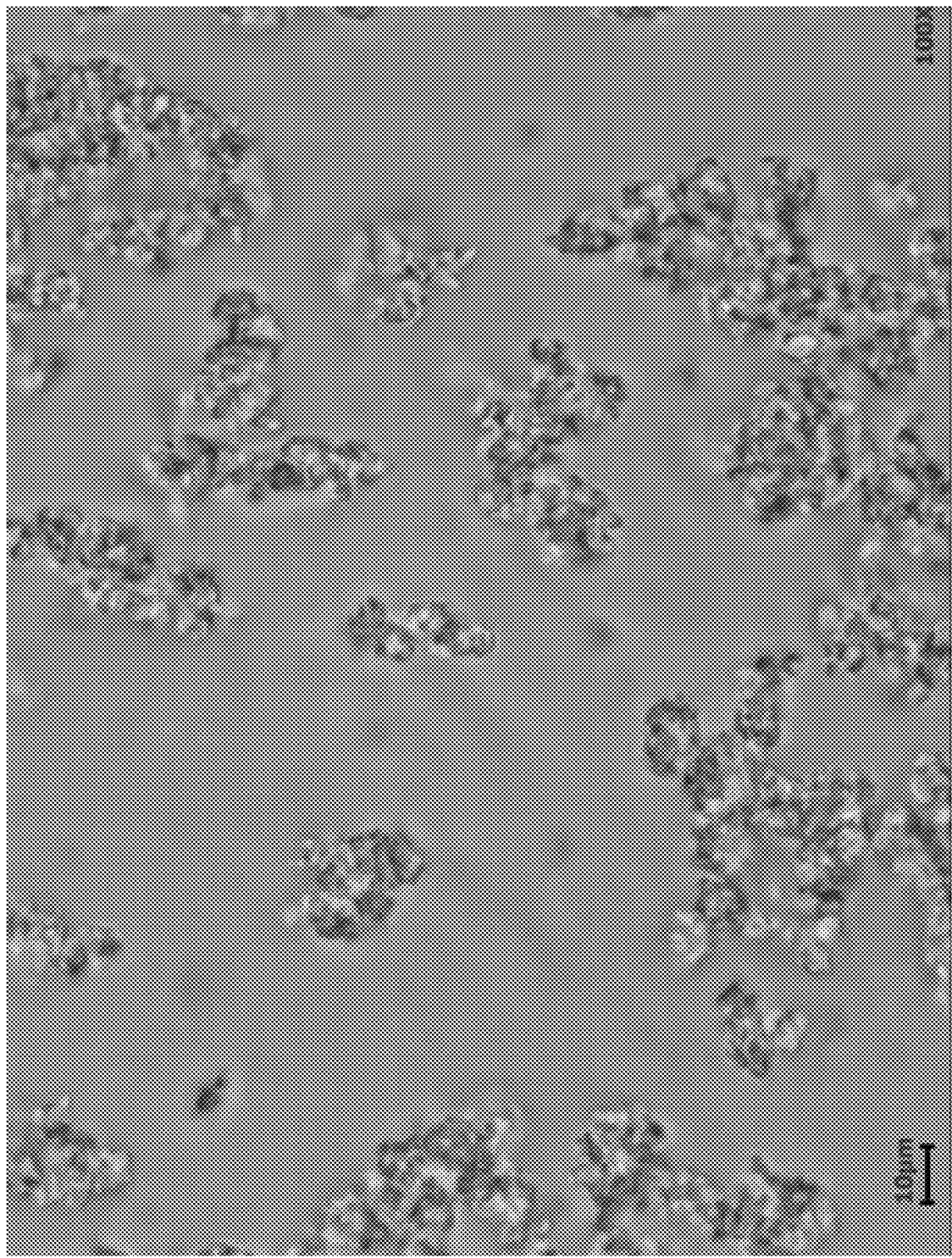
FIG. 3C shows an example of a microscope image of a microfluidic processed composition of quillaja extract, hemp oil, water, and sodium alginate at 1000× magnification.

FIG. 3A shows a 1000× magnification micrograph image of a quillaja extract, hemp oil, water, and sodium alginate composition (Test 2, Pass 1), with a 10 μm scale bar. FIG. 3B shows a 1000× magnification micrograph image of a quillaja extract, hemp oil, water, and sodium alginate composition (Test 2, Pass 2), with a 10 μm scale bar. FIG. 3C shows a 1000× magnification micrograph image of a quillaja extract, hemp oil, water, and sodium alginate composition (Test 2, Pass 3), with a 10 μm scale bar.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for subjecting a subject to an augmented reality (AR) or virtual reality (VR) experience, comprising:
    (a) administering to said subject a composition comprising a cannabinoid compound;
    (b) subsequent to or during (a), using an AR or VR device to subject said subject to said AR or VR experience, wherein said AR or VR device comprises an electronic screen that provides said AR or VR experience to said subject;
    (c) subjecting said subject to emotional freedom technique or eye-movement desensitization and reprocessing; and
    (d) detecting a response of said subject to said AR or VR experience.

2. The method of claim 1, comprising, in (c), subjecting said subject to said emotional freedom technique.

3. The method of claim 1, comprising, in (c), subjecting said subject to said eye-movement desensitization and reprocessing.

4. The method of claim 1, comprising, in (c), subjecting said subject to said emotional freedom technique and said eye-movement desensitization and reprocessing.

5. The method of claim 1, wherein said subject suffers or is suspected of suffering from one or more health conditions.

6. The method of claim 5, wherein said one or more health conditions comprise one or more mental disorders selected from the group consisting of: anxiety disorder, mood disorder, psychotic disorder, eating disorder, impulsive control and addition disorder, personality disorder, obsessive-compulsive disorder, post-traumatic stress disorder, stress response syndrome, dissociative disorder, factitious disorder, tic disorder, and addiction.

7. The method of claim 1, wherein said AR or VR experience is based at least in part on a memory of a historical event of said user.

8. The method of claim 1, wherein said composition comprises a plurality of microcapsules, wherein an individual microcapsule of the plurality comprises (a) at least one cannabinoid compound and (b) at least one terpene compound.

9. The method of claim 8, wherein an individual microcapsule of said plurality comprises at least one cannabinoid compound, and wherein said plurality of microcapsules are not liposomes or micelles.

10. The method of claim 1, wherein said cannabinoid compound comprises cannabidiol (CBD).

11. The method of claim 1, wherein said composition is a liquid composition.

12. The method of claim 1, wherein said composition is a solid composition.

13. The method of claim 1, further comprising orally administering said composition to said subject.

14. The method of claim 1, further comprising topically administering said composition to said subject.

15. The method of claim 1, further comprising, subsequent to (c), administering to said subject an adjusted dosage of said composition, wherein said adjusted dosage is determined at least in part on said response.

* * * * *